United States Patent
Soman et al.

(10) Patent No.: US 9,631,171 B2
(45) Date of Patent: Apr. 25, 2017

(54) MICROSTRUCTURE BIOMATERIALS AND FABRICATION METHODS THEREFOR

(75) Inventors: Pranav Soman, San Diego, CA (US); Shaochen Chen, San Diego, CA (US); David Fozdar, Edmond, OK (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 624 days.

(21) Appl. No.: 13/989,024

(22) PCT Filed: Nov. 22, 2011

(86) PCT No.: PCT/US2011/061968
§ 371 (c)(1),
(2), (4) Date: Aug. 12, 2013

(87) PCT Pub. No.: WO2012/071477
PCT Pub. Date: May 31, 2012

(65) Prior Publication Data
US 2013/0344601 A1    Dec. 26, 2013

Related U.S. Application Data

(60) Provisional application No. 61/416,272, filed on Nov. 22, 2010.

(51) Int. Cl.
| | |
|---|---|
| *C12N 5/00* | (2006.01) |
| *A61L 27/14* | (2006.01) |
| *A61L 27/40* | (2006.01) |
| *A61L 27/52* | (2006.01) |
| *A61L 27/56* | (2006.01) |
| *B29C 67/00* | (2017.01) |

(52) U.S. Cl.
CPC ............ *C12N 5/00* (2013.01); *A61L 27/14* (2013.01); *A61L 27/40* (2013.01); *A61L 27/52* (2013.01); *A61L 27/56* (2013.01); *B29C 67/0081* (2013.01); *A61L 2400/08* (2013.01); *A61L 2400/12* (2013.01); *A61L 2400/18* (2013.01)

(58) Field of Classification Search
None
See application file for complete search history.

(56) References Cited

U.S. PATENT DOCUMENTS

| | | |
|---|---|---|
| 8,034,103 B2 | 10/2011 | Burriesci et al. |
| 2007/0031667 A1 | 2/2007 | Hook et al. |
| 2009/0041978 A1 | 2/2009 | Sogard et al. |

OTHER PUBLICATIONS

Prud'homme, "Fabrication of cellular materials. In 1996 Symposium on Smart Structures and Materials," International Society for Optics and Photonics, p. 331-334, 1996.*

(Continued)

*Primary Examiner* — John S Brusca
*Assistant Examiner* — G. Steven Vanni
(74) *Attorney, Agent, or Firm* — Eleanor Musick; Scott Davison; Musick Davison LLP

(57) ABSTRACT

Methods and systems for fabricating a micro-structured biomaterial include printing a three-dimensional structure using polymerizing radiation modulated by a digital micromirror array to project microstructure patterns into a prepolymer material to form one or more porous scaffold sheets. The microstructure patterns have a unit-cell geometry that exhibits a negative Poisson ratio that is tunable in magnitude.

17 Claims, 19 Drawing Sheets

(56) References Cited

OTHER PUBLICATIONS

Han, "Freeform fabrication of biological scaffolds by projection photopolymerization," J. Manuf. Sci. Eng., vol. 130(2), p. 450-457, 2008.*
Houbertz, "Inorganic-organic hybrid polymers for information technology: from planar technology to 3D nanostructures," Advanced Engineering Materials, vol. 5(8), p. 551-555, 2003.*
Smith, "A novel mechanism for generating auxetic behaviour in reticulated foams: missing rib foam model," Acta materialia, vol. 48(17), p. 4349-4356, 2000.*
Kalita, "Development of controlled porosity polymer-ceramic composite scaffolds via fused deposition modeling," Materials Science and Engineering, vol. C 23, p. 611-620, 2003.*
Masters, "Models for the elastic deformation of honeycombs," Composite structures, vol. 35(4), p. 403-422, 1996.*
Fozdar, "Flash imprint lithography using a mask aligner: a method for printing nanostructures in photosensitive hydrogels," Nanotechnology, vol. 19, 13 pages, 2008.*
Lorato, A. et al., "The transverse elastic properties of chiral honeycombs", Composites Sci. and Tech., 2010, vol. 70, pp. 1057-1063 (Published on-line Jul. 24, 2009).
Aydin, D. et al., "Polymeric Substrates with Tunable Elasticity and Nanoscopically Controlled Biomolecule Presentation", Langmuir, 2010, vol. 26(19), pp. 15472-15480 (Published on-line Sep. 13, 2010).
Fozdar, D.Y., et al., "Three-Dimensional Polymer Constructs Exhibiting a Tunable Negative Poisson's Ratio", Adv. Funct. Mater., Jul. 22, 2011 vol. 21(14), pp. 2712-2720 (Published on-line May 11, 2011).
Alderson, A., "A triumph of lateral thought", Chemistry & Industry, May 17, 1999, pp. 383-391.
PCT/US2011/061968—International Search Report and Written Opinion Jun. 16, 2012, pp. 1-13.
Jackman, R.J., et al., "Design and Fabrication of Topologically Complex, Three-Dimensional Microstructures", Science, New Series, Jun. 26, 1998, vol. 280, No. 5372, pp. 2089-2091.
Lakes, R.S., "No contractile obligations", Nature, 1992, vol. 358, pp. 713-714.
Lakes, R., "A broader view of membranes", Nature, Nov. 29, 2001, vol. 414, pp. 503-504.
Lakes, R., "Foam Structures with a Negative Poisson's Ratio", Science, Feb. 27, 1987, vol. 235, pp. 1038-1040.

* cited by examiner

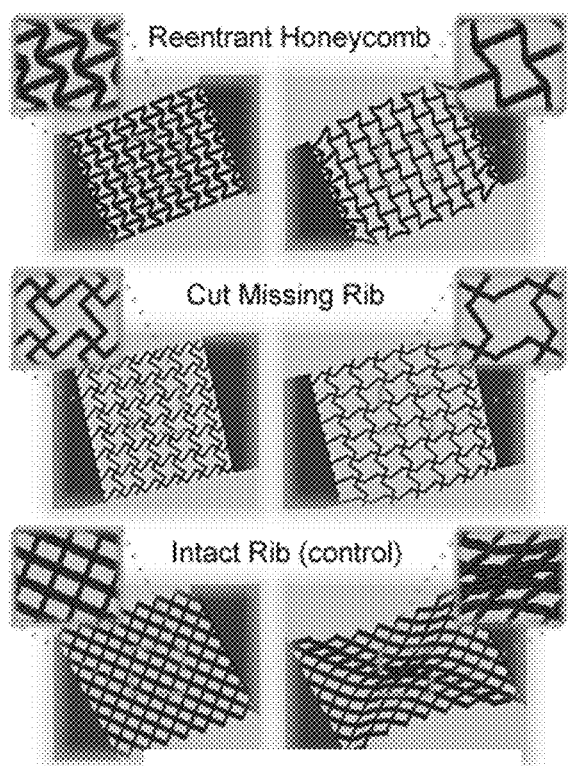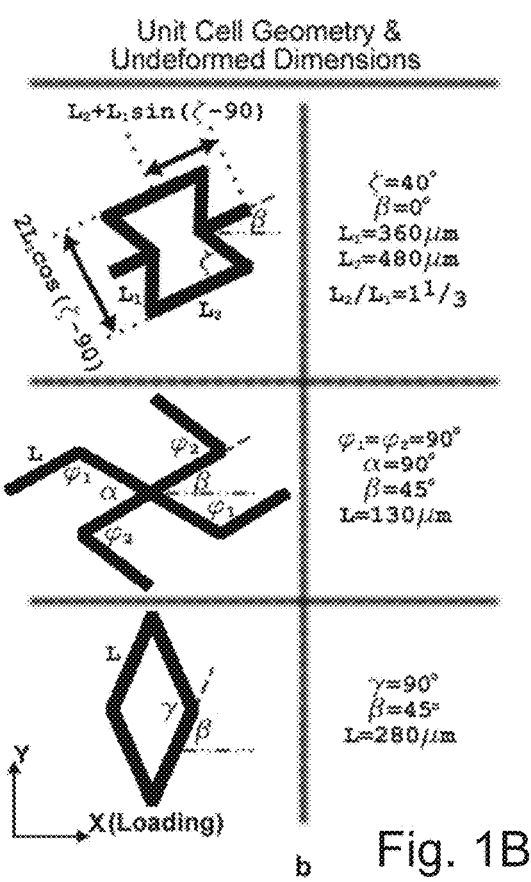
Fig. 1A
Fig. 1B

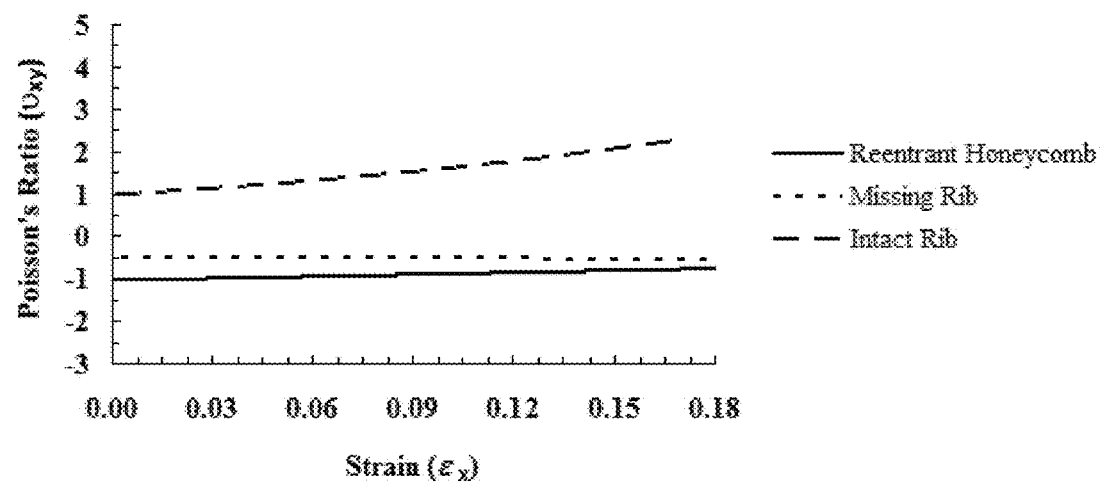
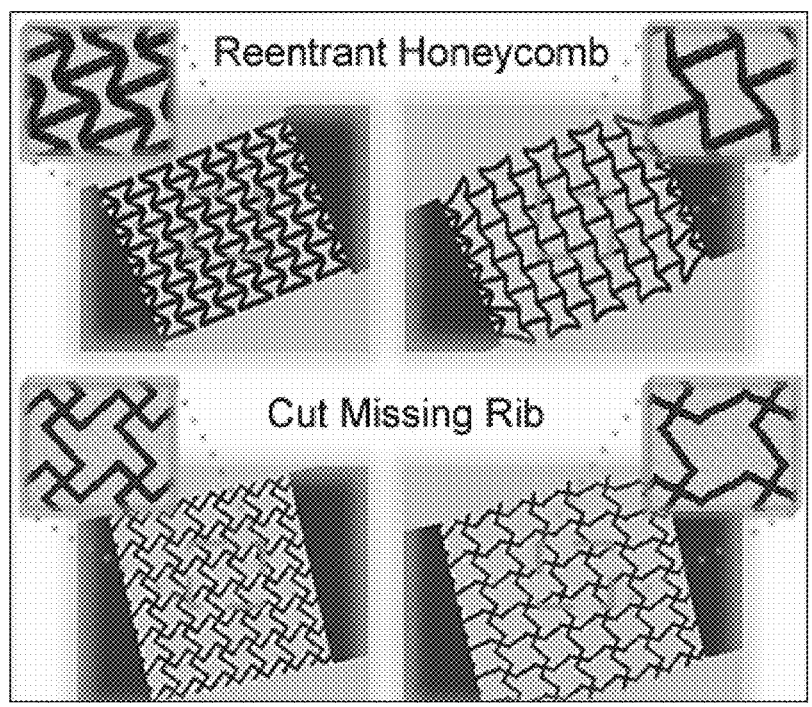
Fig. 7

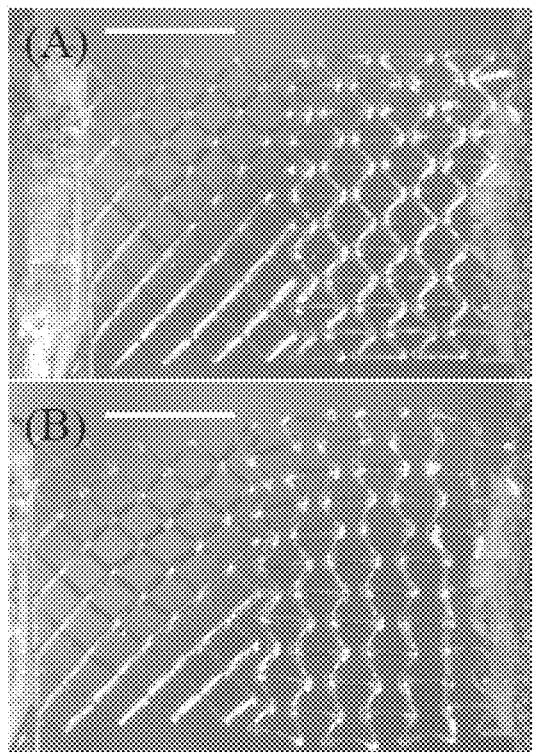
Fig. 11A
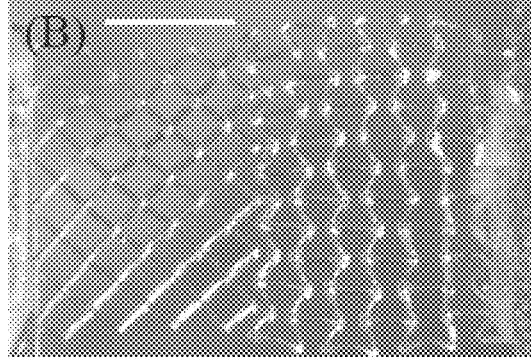
Fig. 11B
Fig. 11D
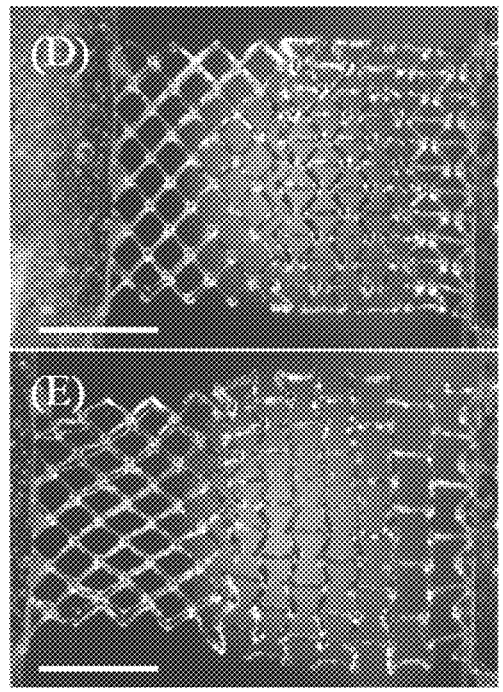
Fig. 11E

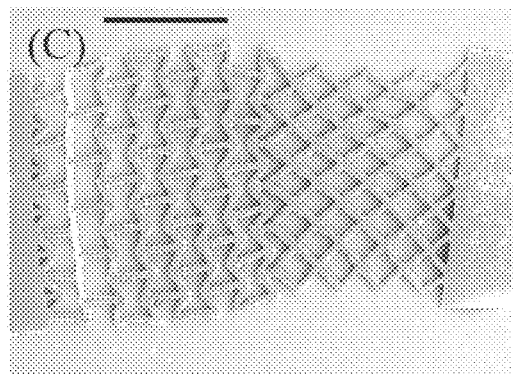
Fig. 11C
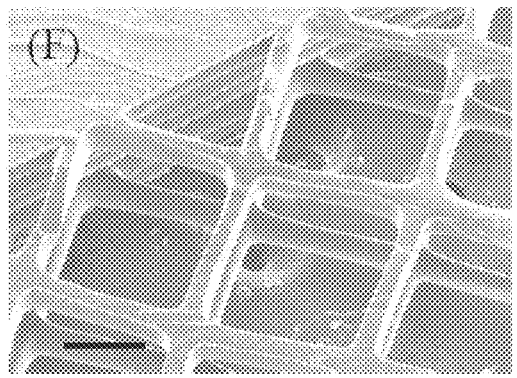
Fig. 11F
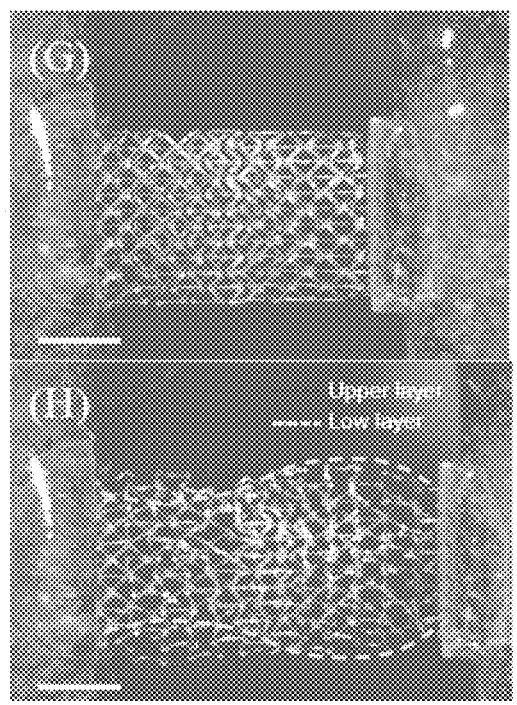
Fig. 11G
Fig. 11H
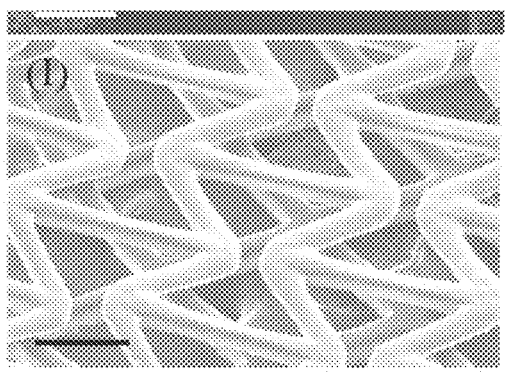
Fig. 11I

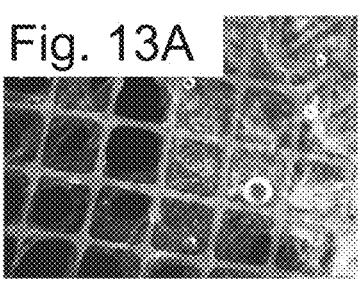
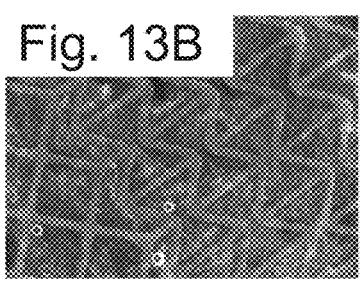
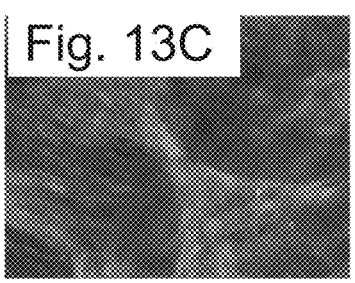
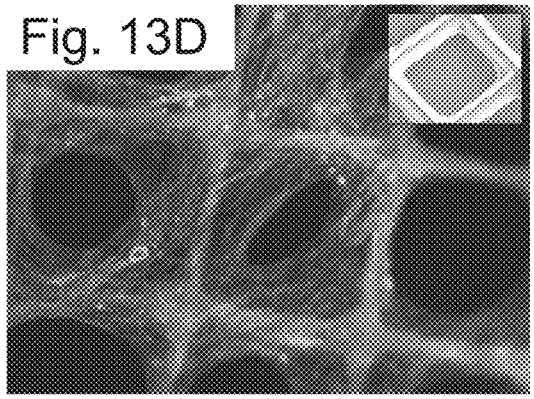
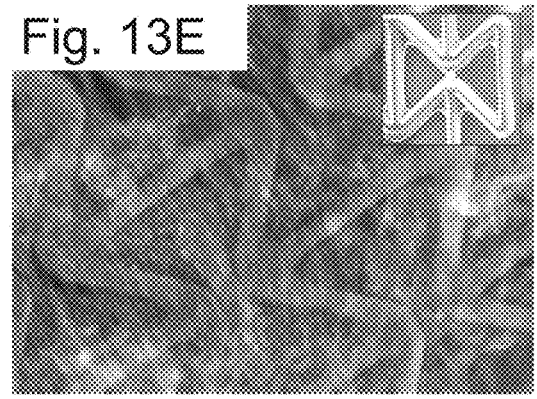

MICROSTRUCTURE BIOMATERIALS AND FABRICATION METHODS THEREFOR

RELATED APPLICATIONS

This application is a 371 National Stage Filing of International Application No. PCT/US2011/061968, filed Nov. 22, 2011, which claims priority to U.S. Provisional Application No. 61/416,272, filed on Nov. 22, 2010. Each application is hereby explicitly incorporated by reference herein in its entirety.

GOVERNMENT RIGHTS

This invention was made with government support under Grant No. R01EB012597 awarded by the National Institute of Biomedical Imaging and Bioengineering (National Institutes of Health (NIH)). The government has certain rights in the invention.

FIELD OF THE INVENTION

This invention relates to devices, techniques and material related to micro-structured biomaterials, and more particularly relates to auxetic micro-structured biomaterials, methods to fabricate these biomaterials and uses of these materials.

BACKGROUND OF THE INVENTION

Tissue engineering has been defined as an interdisciplinary field that applies the principles of engineering and life sciences toward the development of biological substitutes that restore, maintain, or improve tissue function. Three general strategies are employed in tissue engineering: use of isolated cells or cell substitutes, use of tissue-inducing substances, and use of cells placed on or within matrices.

Cells are often implanted or 'seeded' into an artificial structure capable of supporting three-dimensional tissue formation. These structures, typically called "scaffolds", are often critical, both ex vivo as well as in vivo, to allowing cells to influence their own microenvironments. Scaffolds serve one or more of the following purposes: allow cell attachment and migration; deliver and retain cells and biochemical factors; enable diffusion of vital cell nutrients and expressed products; and exert certain mechanical and biological influences to modify the behavior of the cell phase.

To achieve the goal of tissue reconstruction, scaffolds must meet some specific requirements. A high porosity and an adequate pore size are necessary to facilitate cell seeding and diffusion throughout the whole structure of both cells and nutrients. A porous tissue scaffold (construct) should be sufficiently robust to accommodate the forces applied by cells and other outboard mechanical loads imposed during wound healing, blood flow, and patient activity. A scaffold's elastic properties are critical to its efficacy in regenerating tissue and reducing inflammatory responses, and must be matched with the elastic properties of native tissue. The elastic behavior of a porous scaffold can be described by its elastic modulus and Poisson's ratio, which depend on its porosity, the properties of the biomaterial making up the rib structures, and any anisotropic behavior due to the presence of pores. Optimizing these attributes requires control over pore size and geometry with the restriction of arranging the pores so they are open to the environment and completely interconnected.

Although yield strength and stiffness (elastic modulus) are of vital importance in providing the scaffold with satisfactory mechanical integrity, and show power-law behavior with regards to porosity, it does not fully characterize a construct's elastic behavior since it only describes deformation in the loading direction and does not address deformations in the transverse direction.

Poisson's ratio, on the other hand, describes the degree to which a material contracts (expands) transversally when axially strained, and is the property that addresses transverse strains resulting from axial deformations. The Poisson's ratio of virtually every porous biomaterial tissue construct is positive, i.e., it contracts in the transverse direction upon expanding in the axial direction. In some applications, scaffolds having a negative Poisson's ratio may be more suitable for emulating the behavior of native tissues and accommodating and transmitting forces to the host tissue site.

When Poisson's ratio is negative, expansion occurs in both the axial and transverse directions simultaneously. This unusual phenomenon has been show to occur in crystalline materials such as crystalline α-cristobalite $SiO_2$, materials with hinged crystal structures, carbon allotropes, foams, microporous polymers and laminates, and other extreme states of matter. However, nothing has been reported on the fabrication of three-dimensional biomaterial constructs exhibiting a tunable negative Poisson's ratio.

It has been shown that man-made auxetic (negative Poisson's) polymers can be constructed by patterning non-auxetic polymers with an artificial lattice of rib-containing unit-cells (pores). Materials of this sort have been coined, cellular or hinged materials, owing to the fact that their constitutive pore structure can have a sizable effect on their mechanical behavior. Several unit-cell models have been proposed, each having well-defined strain-dependent Poisson's ratios (Poisson's function) described analytically. In the past, auxetic polyurethane foams have been formed by annealing the foams in a compressed state, which naturally causes a re-organization in their cellular microstructure. However, the annealing process renders little practical control over the cellular microstructure comprising the foams, making it very difficult to premeditatedly modulate the strain-dependent behavior of Poisson's ratio. In tissue engineering, one must have the capability to precisely tune the magnitude and polarity (positive or negative) of Poisson's ratio in three-dimensional constructs to match the properties of the specific tissue being regenerated. Moreover, such command over Poisson's ratio must also be attainable in biologically-relevant materials.

The elastic properties of a biomaterial tissue scaffold reflect its ability to handle external loading conditions and must be tailored to match the attributes of the underlying native tissue that it aims to repair. A scaffold's elastic modulus and Poisson's ratio describe how the biomaterial tissue scaffold supports and transmits external stresses to the host tissue site. While the elastic modulus is tunable in scaffolds, the Poisson's ratio of virtually every porous tissue construct is positive. The Poisson's ratio is positive/negative when the material contracts/expands transversally with axial expansion.

BRIEF SUMMARY OF THE INVENTION

The present invention provides a construct having a tunable negative Poisson's ratio (an auxetic construct) that is more suitable than prior art approaches for supporting the external forces imposed upon it.

Techniques, structures, apparatus and materials are disclosed for fabricating micro-structured biomaterials that are auxetic (e.g., exhibit a negative Poisson's ratio) to expand rather than contract transversally when stretched axially. As disclosed herein, some applications, a construct having a tunable negative Poisson's ratio (an auxetic construct) may be more suitable for supporting the external forces imposed upon it by its environment.

In some embodiments, the novel micro-structured biomaterials and methods used to fabricate said biomaterials are auxetic, i.e., exhibit a negative Poisson ratio (expand rather than contract transversally when stretched axially). In various embodiments, the auxetic materials are fabricated using digital micromirror device projection printing from photocurable biocompatible materials.

In some embodiments, the auxetic biomaterials are used in the field of tissue engineering, non-limiting examples of tissue engineering include auxetic cardiac patch and blood vessel repair. In other embodiments, the biomaterials are used for healing wounds, including but not limited to medical sutures. Other uses contemplated herein are those that require scaffolds emulating auxetic tissues. In some embodiments, the auxetic biomaterials are fabricated from traditional polyethylene glycol (PEG).

In some embodiments, a three-dimensional polyethylene glycol scaffold with tunable negative Poisson's ratio is disclosed. In these embodiments, a digital micro-mirror device projection printing (DMD-PP) can be used to print single-layer constructs composes of cellular structures (pores) with special geometries, arrangements, and deformation mechanisms. The presence of the unit-cellular structures tunes the magnitude and polarity (positive or negative) of Poisson's ratio.

In other embodiments, multilayer constructs are fabricated with DMD-PP by stacking the single-layer constructs with alternating layers of vertical connecting posts. The Poisson's ratio of the single-layer and multilayer constructs can be determined from strain experiments which show (1) that the Poisson's ratios of the constructs are accurately predicted by analytical deformation models and (2) that no slipping occurs between layers in the multilayer constructs and the addition of new layers does not affect Poisson's ratio.

BRIEF DESCRIPTION OF THE DRAWINGS

FIG. 1A illustrates stress-strain simulations of single-layer PEG constructs composed of unit-cells having, from top to bottom, the reentrant honeycomb, cut missing-rib, and intact-rib architectures.

FIG. 1B shows the unit-cell geometry and relevant dimensional parameters for each of the three unit cell types shown in FIG. 1A.

FIGS. 2A, 2B and 2C are single-layer PEG constructs; FIGS. 2D, 2E and 2F are double-layer PEG constructs; and FIGS. 2G, 2H, and 2I are triple-layer reentrant PEG constructs.

FIG. 7 is a plot of Poisson's ratio as a function of true strain as given by the analytical models.

FIGS. 11A-11I are optical and scanning electron microscope (SEM) images of the expansion (contraction) of hybrid scaffolds, where FIGS. 11A and 11B are optical images of single-layer scaffolds, and FIGS. 11D and 11E are optical images of double-layer PEG scaffolds, in undeformed and deformed states, respectively. FIGS. 11C and 11F are SEM images single layer and double layer hybrid scaffolds, respectively. FIGS. 11G and 11H are optical images of showing NPR behavior on selective regions of top and bottom scaffolds and FIG. 11I is a SEM image showing two layer scaffolds with no supporting posts layer.

FIGS. 13A-13E are fluorescence microscopic images of human mesenchymal stem cells, where FIGS. 13A and 13C show the Positive Poisson ratio (PPR) region and FIGS. 13B and 13D show the Negative Poisson ratio region. Scale bars in FIGS. 13A and 13B represent 200 µm and 100 µm in FIGS. 13C and 13D. The results illustrate that bovine aortic smooth muscle cells not only adhere and proliferate on the struts of the reentrant scaffolds, but also fill up the spaces between the struts.

FIGS. 14A and 14B are side views and FIGS. 14C and 14D are top views of bead loading near the PPR region. These figures demonstrate contraction of the PPR region while expansion of the NPR region. FIGS. 14E and 14F are top views of bead loading near the NPR region and demonstrate conformation of the NPR region onto the bead surface.

DETAILED DESCRIPTION OF THE EXEMPLARY EMBODIMENTS

The present invention provides materials and methods for formations of three-dimensional biomaterial constructs in polyethylene glycol (PEG) that exhibit determinate (predictable) in-plane negative Poisson's ratios. Auxetic behavior was achieved by patterning specially-arranged unit-cellular structures with a digital micro-mirror device projection printing (DMD-PP) system (FIG. 10). Unit-cell geometries and spatial-arrangements were designed from existing analytical models that predict strain-dependent negative Poisson's behavior. An acrylated-PEG hydrogel was used, in part because of its use in porous tissue scaffolds seeded with bone marrow-derived progenitor cells and its ability to encapsulate timed-release biomolecules that stimulate tissue growth.

Harnessing the capabilities of DMD-PP micro-stereolithography, we designed and developed three-dimensional biomaterial scaffolds having negative strain-dependent in-plane Poisson's ratios. These biomaterials are tunable by varying pore (unit-cell) structure and can be easily described (and predicted) by analytical models.

Figure 10A:
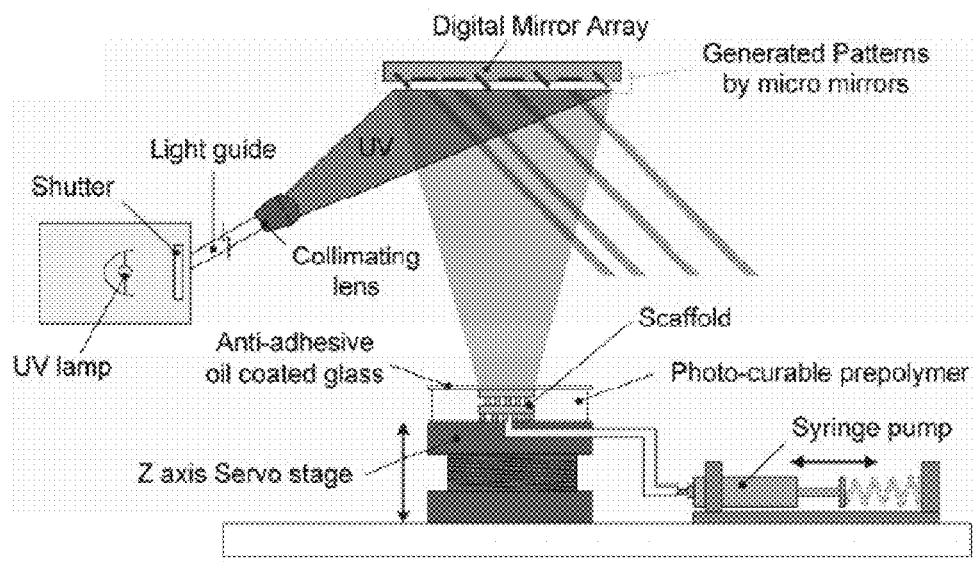
FIG. 10A is a schematic of the digital micromirror device micro-stereolithography system (DMD-SL) used for fabricating 3D porous biomaterial constructs having tunable hybrid NPR-PPR scaffolds.
Figure 10B:
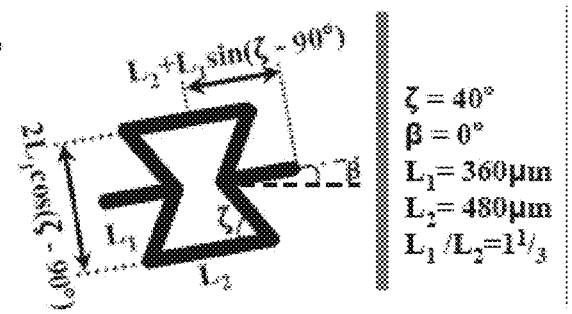
FIGS. 10B and 10C illustrate unit-cell geometry and relevant dimensional parameters having the negative Poisson ratio (NPR) and positive Poisson's ratio (PPR) architectures, respectively.

As discussed herein, we have constructed single-layer and double-layer PEG scaffolds, which exhibited tunable in-plane negative Poisson's ratios. The single-layer constructs were designed from analytical models found in the literature, and were found to have Poisson's ratios that were consistent with the models. The double-layer scaffolds were fabricated by assembling single-layer constructs in a layer-by-layer fashion, and contained pores that were accessible to the environment and completely interconnected as desired in a biomaterial tissue scaffold. The double-layer scaffolds exhibited strain-dependent Poisson's ratios that were very similar to those of the single-layer constructs, which suggested that adding additional layers to a scaffold does not markedly affect the tunability of the Poisson's ratio. Finally, we used our multi-layer scaffold design scheme to fabricate a triple-layer reentrant scaffold with precise vertical alignment, which showed that our design methodology can be used to make a biomaterial construct with multi-layers.
Exemplary PEG Constructs FIG. 10A is a schematic of the Digital Micromirror Device Stereolithography (DMD-SL) system used for fabricating the hybrid Poisson's ratio scaffold. The geometry and relevant dimensions of unit cells with Negative Poisson's Ratio (NPR) and Positive Poisson's Ratio (PPR) behavior were used to make dynamic photo-images for the DMD-SL system. The intact rib model (PPR) and the reentrant honeycomb design (NPR) was adapted from models reported in literature. The NPR structure is formed by changing the four side angles (angle $\zeta$) between the vertices (ribs) in a six-sided honeycomb, with some additional modifications to the ratio of the two rib lengths, $L_1$ and $L_2$. We applied strains along the X-X axis, (FIG. 10B, $\beta$=0), however strain-dependent Poisson's ratio can also be tuned by simply changing the direction of loading (anisotropic) relative to the orientation of the unit-cell shape (angle $\beta$ in FIG. 10B). We choose angle $\zeta$=40°, but this angle can be altered to tune the magnitude of Poisson's ratio Unlike the NPR reentrant structure, the PPR intact rib structure does not dependent on the direction of loading. The material walls of each model are denoted as struts, and have a rectangular cross-section approximately 50 microns in width and 100 microns in depth. The arrangement of the struts defines unit-cell shape and encloses pores with well-defined geometries. Rectangular slabs of material were incorporated at the ends of each porous sheet to ensure the mechanical integrity of the sheet for handling during strain testing. The specific location and arrangement of the struts shown in FIG. 10D imparts NPR and PPR character to the scaffold by virtue of a combination of rib flexure, stretching, and angular deformations.

One of the main reasons that tissue engineering efforts over the last 20 years have yielded only a handful of products is that most technologies fail to translate and scale-up into a clinically relevant end-application. The present invention uses DMD-SL (digital micro-mirror-stereolithography) to create a stepper system in which the stage may be translated within the X-Y plane to serially expose multiple adjacent areas with a pattern having micro-scale resolution to produce a continuous scaffold sheet of clinically relevant size. Similar exposure sequences using precision X-Y stepper stages are well known in the integrated circuit fabrication field. In this case, we have stitched a pattern (2.5 mm×2.5 mm) into a 3×4 format, to make a scaffold patch of about ~8 mm×10 mm. The inventive technique can be used to scale up micro-scale scaffolds to virtually any desired size with the use of a servo stage and glass cover having sufficient area to support the continuous scaffold sheet.

Single-layer PEG constructs were tested using a custom-made stage and PPR/NPR regions on the same scaffold were analyzed. FIGS. 11A-11I are optical and scanning electron microscope (SEM) images of the expansion (contraction) of hybrid scaffolds constructed from polyethylene glycol (PEG) biomaterial. Scales are 1 mm for FIGS. 11A-11E and 11G-11H and 100 microns for FIGS. 11F and 11I.

FIGS. 11A, 11B, 11D and 11E are the optical images for single layer and dual layer hybrid scaffolds, respectively, in their undeformed and strained states after application of the axial loading. FIGS. 11C and 11F are SEM images single layer and double layer hybrid scaffolds, respectively. Two-layer scaffolds were assembled by connecting single-layer constructs with alternating layers of vertical posts. FIGS. 11G and 11H are optical images of showing NPR behavior on selective regions of top and bottom scaffolds.

With axial loading, the PPR regions on single-layer scaffolds contract, while the NPR regions transversely expand, demonstrating a hybrid NPR/PPR behavior on a single scaffold. To determine if addition of multiple layers would alter the Poisson's ratios response relative to the hybrid single-layer scaffolds, a two-layer three-dimensional scaffold was developed by stacking two single-layer scaffolds with a layer of vertical posts.

The vertical alignment of the cellular layers is precise, making it difficult to distinguish multiple layers from the optical images. However, the SEM image in FIG. 11F show the two separate layers in the magnified angle views. These multi-layer hybrid scaffolds continue to exhibit similar behavior compared to single-layer NPR-PPR scaffold.

The flexibility of this design approach was demonstrated using DMD-SL to design and build a two layer scaffold, with NPR geometry on the left part of the top layer and right part of the bottom scaffold. Optical images demonstrate how the NPR parts in both top and bottom layer expand laterally, while the PPR parts shrink with axial loading (FIGS. 11A-11I). Optical images show minor differences in elastic behavior of these scaffolds, probably because of lack of the connecting post layer for these scaffolds.

Figure 12A:
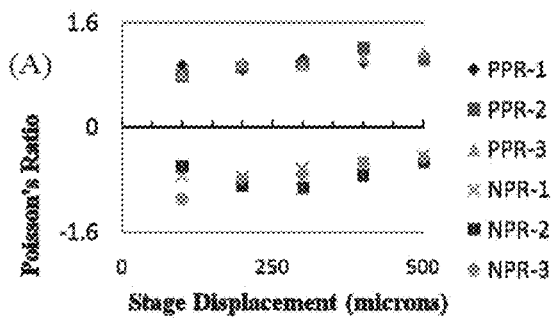
FIGS. 12A-12D provides experimental values of Poisson's ratio as a function of (A) stage displacement for single-layer [0-500 microns] (B) true strain for a single-layer [0-0.3] (C) true strain for single-layer [0-0.6] and (D) true strain for two-layer scaffolds. Three strain-dependent experiments were performed for each type of single-layer construct and two experiments were performed for each two-layer construct; each strain test was conducted with a different sample. Separate experiments are denoted by color in the plots.
Figure 12C:
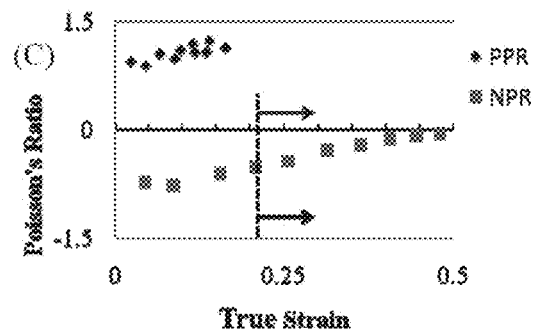
Figure 12B:
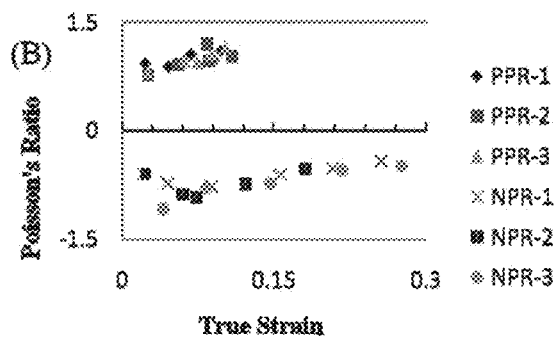

FIG. 12A plots the Poisson's ratios of both the PPR and NPR regions on a single-layer scaffold as a function of stage displacement. Poisson's ratios of the hybrid constructs were calculated by measuring the overall strains in the x- and y-directions. The experimental Poisson's ratios for the single-layer hybrid scaffold showed slight increase for both PPR part (0.7 to 1.2) as well as NPR parts (−1.1 to −0.5) for increasing values of stage displacement. Total true strain was determined by summing contributions to total true strain from the application of incremental true strains. The strain-dependent Poisson's ratio data for the hybrid scaffold matched the analytical models reported in the literature and our deformation simulations, as shown in FIG. 12B.

Figure 10C:
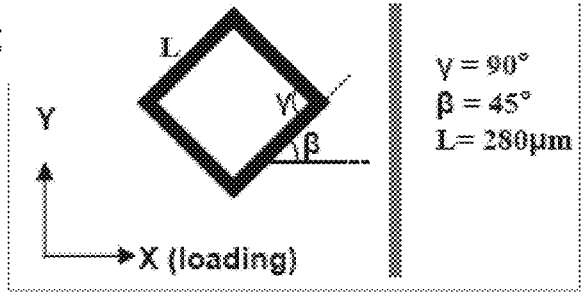
Figure 10D:
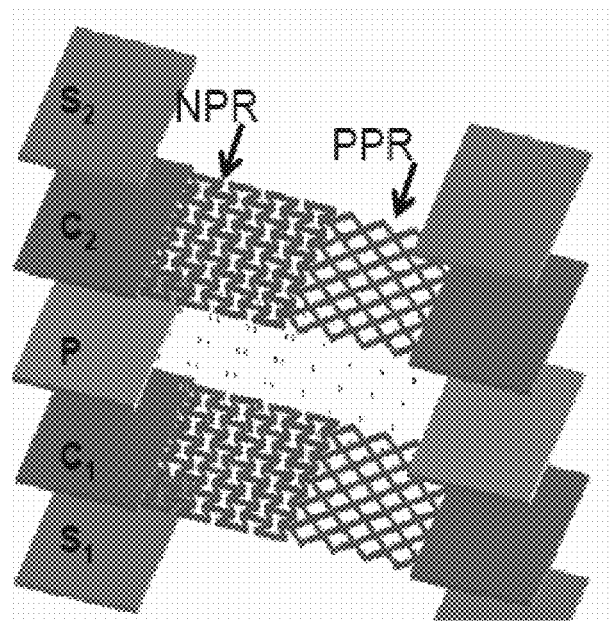
FIG. 10D is a schematic of the double-layer auxetic scaffolds assembled by stacking single-layer cellular constructs with a connecting layer of vertical posts

The simple hinging model reported in the literature, states that the magnitude of the negative Poisson's ratio depends upon both $\zeta$ and the ratio $L_2/L_1$. From the optical images for the NPR region, at zero strain, angle $\zeta$ is approximately 40° ($L_2/L_1=1.33$) and therefore, in our case, the magnitude of the lateral expansion (NPR behavior) solely depends on angle $\zeta$ as it varies with increased axial strain. Our experimental values (−1.1 to −0.5) are similar to those predicted by the analytical model (−1 to −0.7) for the reported axial strains (FIG. 12B). The single-layer intact rib constructs demonstrated experimental Poisson's ratios which varied from slightly below 0.7 to over 1.2 in a linier fashion for axial strains from approximately 0-0.3. In our case, the PPR part had $\gamma=90°$ and $\beta=45°$ (FIG. 10C). The optical images for the intact rib or PPR part of the hybrid scaffold confirm the Smith model, since most of the deformation is caused by hinging of angle $\gamma$, causing the square pore shape to become oblong.

In one of the experiments, we applied a strain of up to 0.5 value. The results are shown in FIG. 12C. However, in this case as $\zeta \geq 90°$, the NPR part of the scaffold relinquishes its auxetic or NRR behavior and behaves like a normal material. Overall, the Poisson's ratio results for both PPR and NPR regions were determinate and tunable by virtue of their well-defined cellular meshworks, and appear to be consistent for all the single-layer hybrid scaffolds (FIG. 12B). The geometry and spatial arrangement of the pores controlled the polarity and magnitude of the Poisson's ratio of the hybrid scaffolds, and the results matched well with previous stress-strain analytical models. This demonstrates the flexibility of the DMD-SL platform for tuning the magnitude and polarity of the Poisson's ratio by simply imparting specific strut configuration.

Figure 12D:
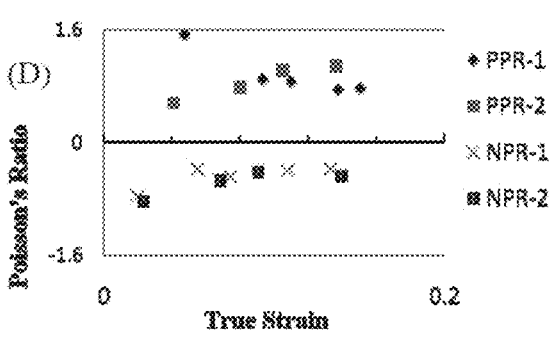
Figure 14A:
FIGS. 14A-14F are optical images of out-of-plane loading on hybrid scaffold. A 2 mm ceramic bead was vertically pushed against the hybrid scaffold and top and side view optical images were captured.
Figure 14B:
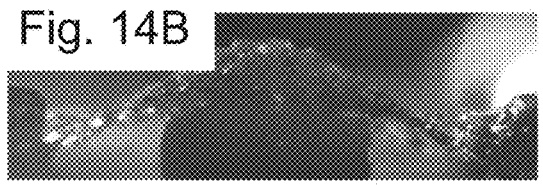
Figure 14C:
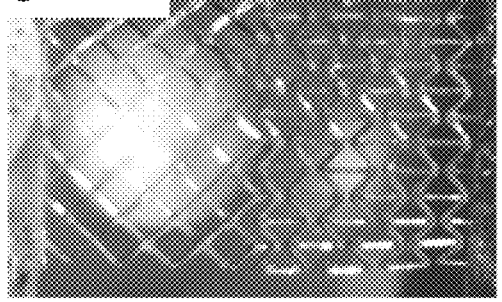
Figure 14E:
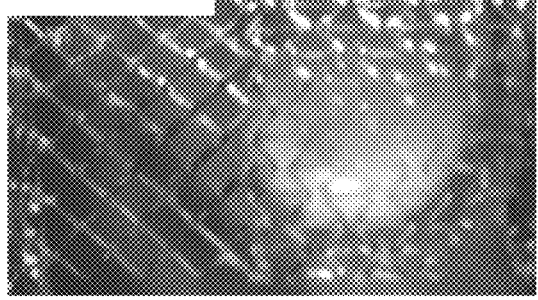
Figure 14D:
Figure 14F:
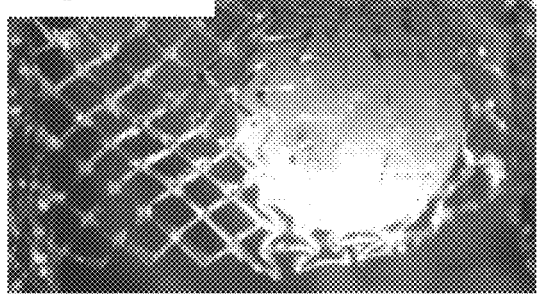

Using the fabrication approach depicted in FIGS. 10D-H, we built a double-layer hybrid scaffold, with two separate hybrid layers ($C_1$ and $C_2$) connected by a alternating layer of vertical posts (P). For the two layer hybrid scaffolds, the NPR and PPR regions exhibit a Poisson's ratio between −0.8 to −0.3 and 1.5 to 0.7 respectively, for true strains up to 0.2 (FIG. 12D). Comparing the optical images of FIGS. 11A, 11B, 11D, 11E, 11C and 11F between the single-layer and double-layer hybrid scaffolds, the deformation of the individual units appears similar, in terms of the deformation mechanisms and appeared to deform equally and in tandem without slipping. Although adding an additional layer did not alter the strain-dependent Poisson's ratio to a large degree, slight discrepancy can be observed in the Poisson's ratios between the single-layer and double-layer hybrid scaffolds. This demonstrates that the addition of the second cellular layer appeared to have little influence on Poisson's ratio behavior of the scaffolds, thus opening possibilities to tune Poisson's ratio in a layered configuration.

FIG. 1A shows the simulated deformation of single-layer PEG constructs composed of arrays of constitutive unit-cells having, from top to bottom, (1) re-entrant honeycomb, (2) cut missing rib, and (3) intact rib architectures. The simulations show the elastic deformation of the constructs resulting from the application of a tensile "pulling" axial load. The reentrant and cut missing rib designs were adapted from models reported in the literature and are auxetic. The intact rib model is not auxetic (positive Poisson's ratio), and was used as a control in our tests of Poisson's ratio. The material walls of each model are denoted as ribs, and have a rectangular cross-section approximately 40 microns in width and 100 microns in depth. The arrangement of the ribs defines unit-cell shape and encloses pores with well-defined geometries, which we desire in a biomaterial tissue construct.

FIG. 1B highlights the geometry and relevant dimensions of each unit-cell type shown in FIG. 1A. Rectangular slabs of material were incorporated at the ends of each porous sheet to ensure the mechanical integrity of the sheet for handling during strain testing.

In the unit-cell models of FIGS. 1A and 1B, the position and arrangement of the ribs relative to one another engender a negative and magnified strain-dependent Poisson's ratio by virtue of a combination of rib bending (flexure), stretching, and hinging (angular deformations). The degree to which each mode of deformation contributes to the elastic properties of a cellular meshwork depends on unit-cell geometry and the material properties of the ribs. Poisson's ratio is usually strain-dependent for cellular materials, but unit-cell shape and orientation relative to the direction of loading (angle $\beta$) for each unit-cell in FIG. 1B also plays a role in the magnitude and polarity of the Poisson's ratio. The way the constitutive unit-cell of a cellular material responds to shear loads is known as the off-axis elastic response of the unit-cell. Accordingly, in this biomaterial, Poisson's ratio is directional (anisotropic) if it varies in magnitude or polarity with the direction of loading.

The reentrant structure (FIGS. 1A & 1B, top) is formed by changing the four side angles (angle $\zeta$) between the vertices (ribs) in a six-sided honeycomb (hexagon), along with some additional modifications. Two rib lengths, $L_1$ and $L_2$, constrain the dimensions of the unit-cell, including angle $\zeta$ (the value of angle $\zeta$ is set by the rib-length ratio and is not arbitrarily set), and the ratio of the two rib lengths has a sizable influence on Poisson's ratio. The reentrant mesh demonstrates a high degree of anisotropy, with uniform in-plane expansion (compression) demonstrated only when normal stresses are applied ($\sigma_x$, $\sigma_y$) with respect to the orientation shown in FIG. 1B ($\beta=0°$). The reentrant structure yields to shear stresses imposed by "diagonal" loads, leading to states of strain that are not auxetic. Varying angle ζ alters the magnitude of Poisson's ratio, which gives Poisson's ratio its strain-dependent response.

The missing rib model (FIGS. 1A and 1B, middle) is formed by removing select ribs from the intact model, so that the intact form then has "missing" ribs. Like the reentrant mesh, the missing rib mesh demonstrates auxetic behavior that varies with changes in unit-cell dimensions, particularly angles α and β (FIG. 1B); however, unlike the reentrant model, the off-axis properties of the missing rib unit-cell are not well documented. Changes in the central angles, α and β, play a critical role in imposing the strain-dependent response of the missing rib unit-cell.

The intact rib (control) meshwork (FIGS. 1A and 1B, lower) has a positive Poisson's ratio regardless of the direction of loading. As with the missing rib model, the off-axis response of the intact rib unit-cell is not well documented. The strain-dependent nature of the Poisson's ratio for the intact unit-cell is predominately caused by changes in angle γ resulting from increasing values of axial strain.

Figure 2A:
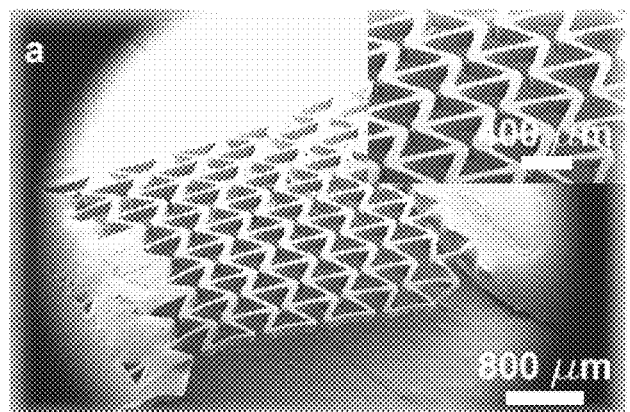
FIGS. 2A-2I are scanning electron micrographs of cellular polymer scaffolds constructed from polyethylene glycol (PEG) with tunable negative Poisson's ratios. The constructs were fabricated using digital micromirror device micro-stereolithography systems.
Figure 2B:
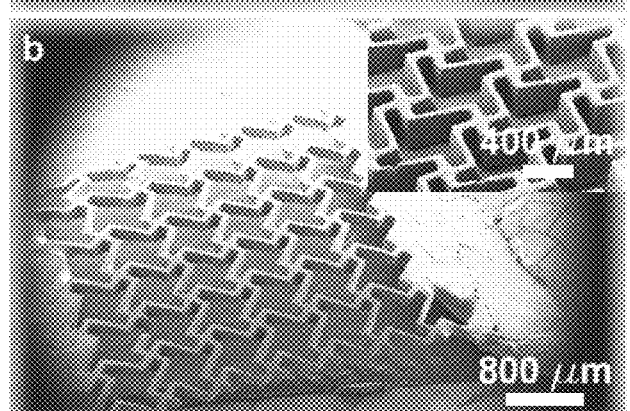
Figure 2C:
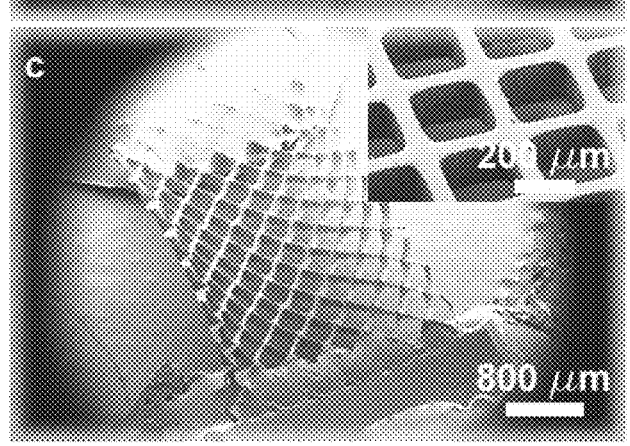
Figure 2D:
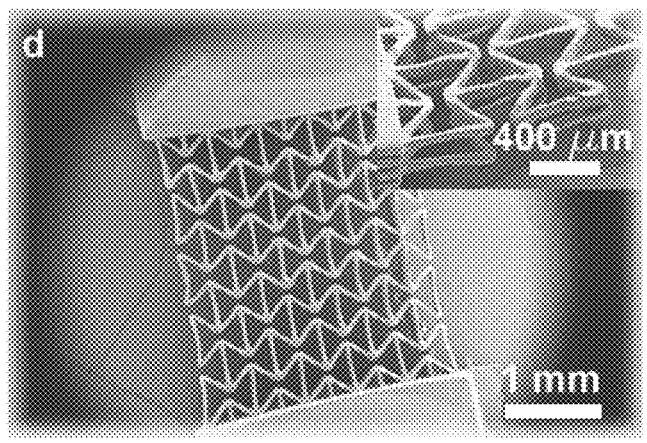
Figure 2E:
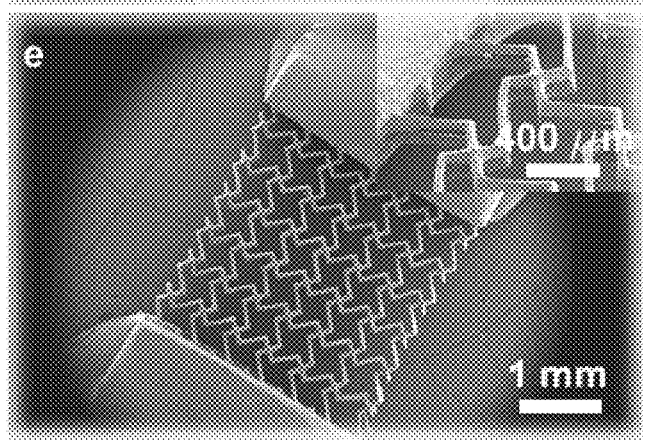
Figure 2F:
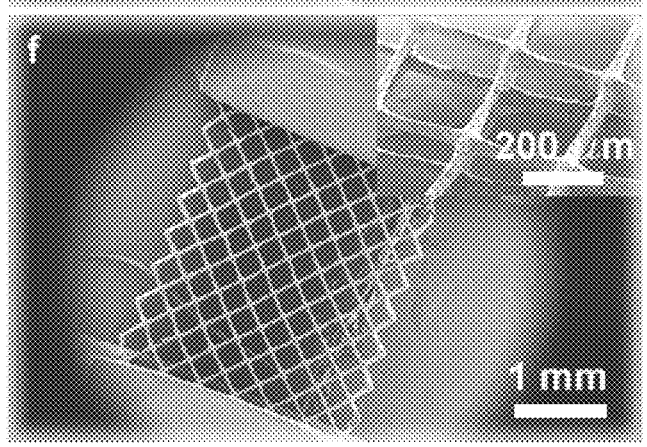
Figure 2G:
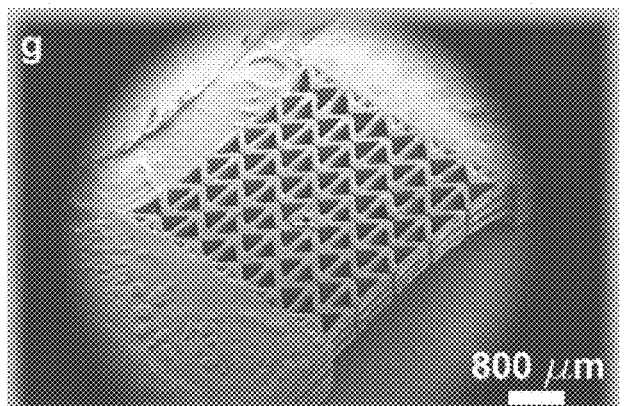
Figure 2H:
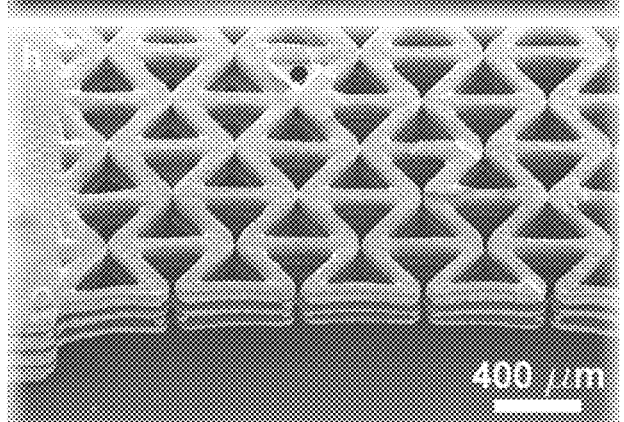
Figure 2I:
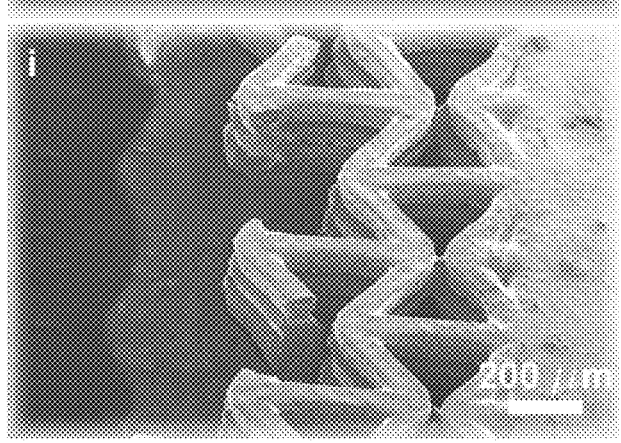

Single-layer PEG constructs were patterned with the unit-cell lattices depicted in FIGS. 1A and 1B, with the resulting structures shown in FIGS. 2A-2I. The constructs were fabricated using digital micromirror device micro-stereolithography systems. FIGS. 2A, 2B and 2C are single-layer PEG constructs; FIGS. 2D, 2E and 2F are double-layer PEG constructs; and FIGS. 2G, 2H, and 2I are triple-layer reentrant PEG constructs. Blocks of PEG were connected to the ends of the constructs to provide mechanical stability in handling and strain testing. Single-layer constructs are composed of a lattice of specially-arranged unit-cells having well-defined geometries resembling the reentrant honeycomb (shown in FIGS. 2A, 2D, 2G, 2H and 2I), missing rib (shown in FIGS. 2B and 2D), and intact rib architectures (shown in FIGS. 2C and 2F). Constructs having the reentrant and missing rib unit-cells exhibit a negative Poisson's ratio while those having the intact rib structure have a positive Poisson's ratio. The strain-dependent behavior of the Poisson's ratios are well-described by analytical models. Multi-layer constructs (two-layer and triple-layer) were assembled by connecting single-layer constructs with alternating layers of vertical posts. The ribs making up the unit-cells enclose pores having a well-defined shape, and the multi-layer constructs have pore arrangements that are accessible to the environment and demonstrate 100% interconnectivity as desired in a biomaterial tissue construct. Strain tests were conducted to determine the Poisson's ratios of the single-layer constructs as a function of true (instantaneous) axial strain. Testing was implemented by fixing one end of the scaffolds while applying an axial tensile load at the other end. Poisson's ratios were approximated by measuring the axial and transverse deformations of the overall scaffold meshworks.

Figure 3A:
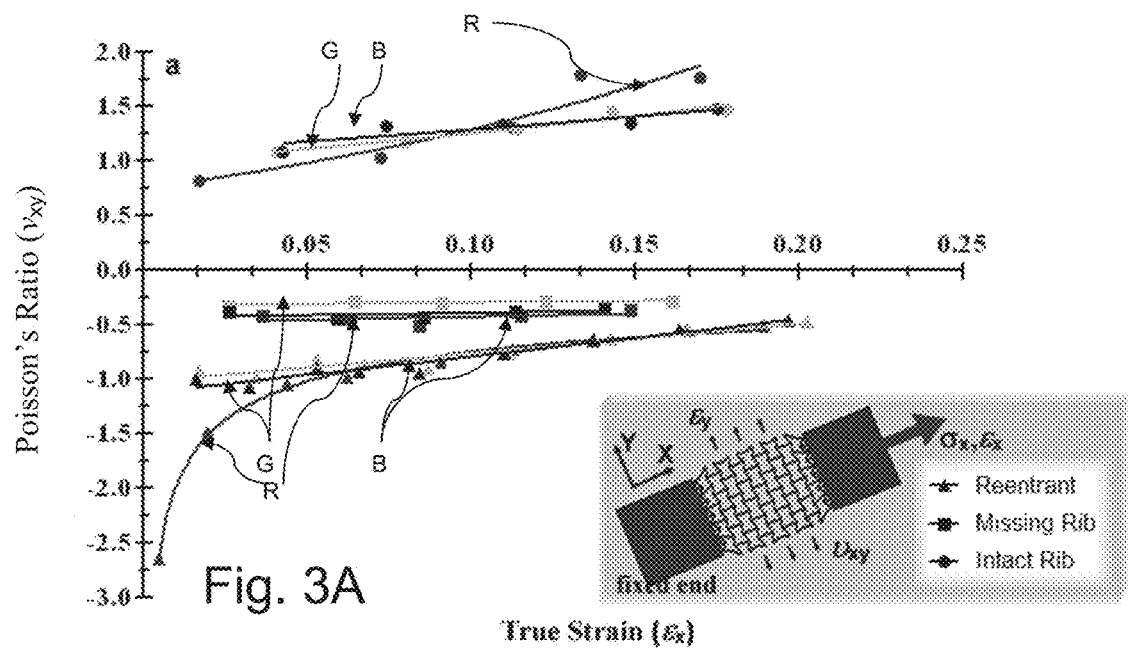
FIGS. 3A and 3B illustrate measured Poisson's ratio as a function of true strain for the single-layer and double-layer constructs, respectively, composed of the reentrant, missing rib, and intact rib unit-cell geometries.

FIG. 3A is a plot of the Poisson ratios of the single-layer constructs for values of true strain ($\epsilon=\delta L/L$ where $\epsilon$ is true strain, L is length, and $\delta L$ is incremental change in length) from 0 to approximately 0.2 for each unit-cell type.

Poisson's ratio ($\upsilon_{xy}$) was calculated by $\upsilon_{xy}=\epsilon_y/\epsilon_x$, where x- is the loading direction and y- is the lateral (transverse) direction. Three experiments were conducted for each unit-cell type, and are denoted by "R", "G" & "B" in the plots in FIG. 3A, where reentrant type is indicated by a triangle (▲), missing rib type by a box (■) and intact type by a circle (●). Each strain test was performed with a different sample.

Figures 4A, 4B:
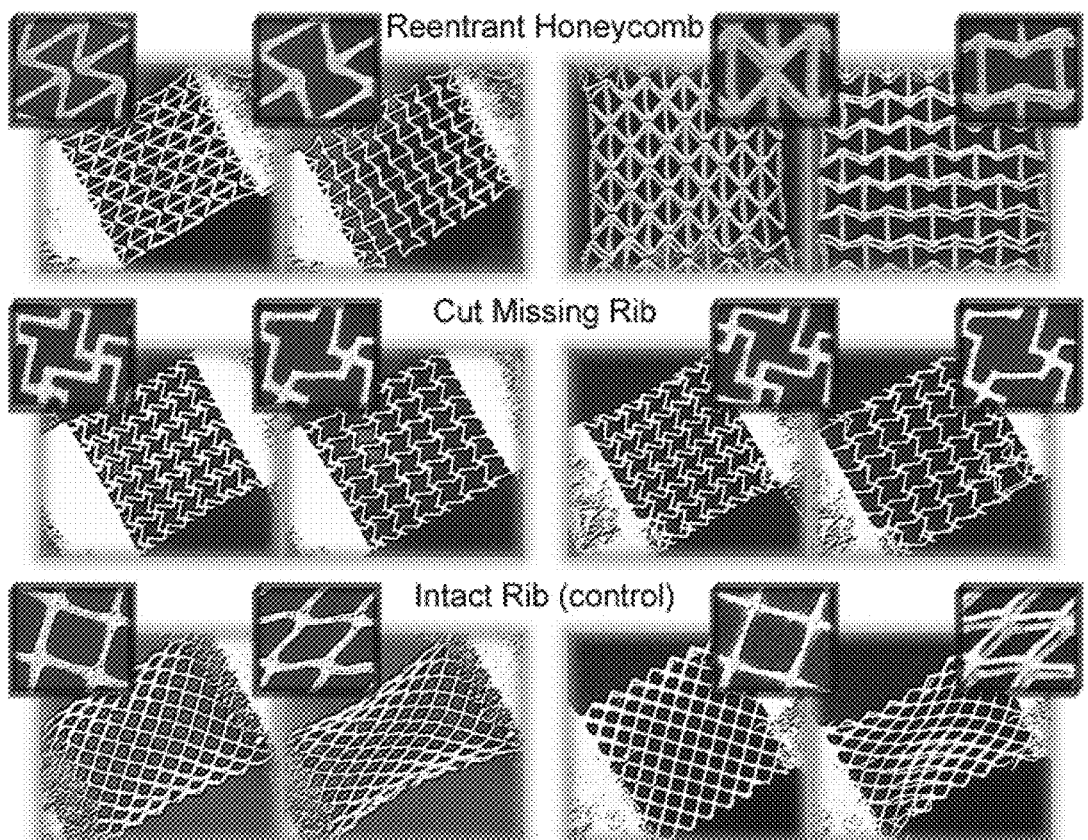
FIGS. 4A and 4B optical images of the expansion (contraction) of the single-layer and double-layer PEG scaffolds, respectively, in response to an applied axial strain. The side-by-side images show the scaffolds in their (left) undeformed and (right) deformed strain states. The insets show deformation in the individual unit-cells (and the pores enclosed by the ribs).

FIGS. 4A and 4B illustrate the mechanical responses of the single-layer constructs resulting from the application of the axial tensile load. The side-by-side optical images show the constructs in their undeformed and strained states, and were taken from one of the three tests performed for each unit-cell. The insets depict deformations in the individual pores (unit-cells).

As shown in FIG. 3A, the Poisson's ratios of the single-layer reentrant and missing rib constructs were negative while the intact rib construct (used as a control) was not-auxetic for the values of true strain that were tested (0-0.2). Because PEG is not auxetic, our results show that pore geometry (or unit-cell shape) induced auxetic behavior as predicted by analytical models and our deformation simulations.

The experimental Poisson's ratios for the single-layer reentrant construct decreased linearly (in magnitude) from approximately −1 to approximately −0.5 for increasing values of true axial strain from 0-0.2 (FIG. 3A). This corresponds to a linear rate of decrease in Poisson's ratio of approximately +3 ($\Delta\upsilon_{xy}/\Delta\epsilon_x$) for $\zeta \geq 40°$ (Δ denotes change, such that for general parameter X where subscript "0" represents the undeformed or initial value).

According to the simple hinging model reported by Gibson et al., *Cellular solids: structure and properties,* Cambridge University Press, Cambridge, UK, 1997, axial strain causes solely a change in angle ζ while the magnitude of the negative Poisson's ratio depends upon both ζ and the ratio $L_2/L_1$, where the rib length ratio is assumed to stay constant. Accordingly, if you examine the optical images for the reentrant sheet in FIG. 4A, it is evident that there is predominately hinging of angle ζ with little flexure or change in rib length. For $L_2/L=1.33$, which gave an undeformed angle ζ of approximately 40°, the hinging model yields a theoretical Poisson's ratio of approximately −1 at zero strain that linearly decreases to about −0.7 for axial strains of 0-0.2. This corresponds to a linear decrease in Poisson's ratio (in magnitude) at a rate of approximately −2($\Delta\upsilon_{xy}/\Delta\epsilon_x$) for $\zeta \geq 40°$.

Moreover, axial strains between 0-0.2 theoretically cause angle ζ to increase from 40° to approximately 52° (changes in angle ζ were not measured experimentally). Thus, our experimental values (−1 to −0.5) are very similar to those predicted by the analytical model (−1 to −0.7) for axial strains of 0-0.2.

In one of the reentrant experiments, a Poisson's ratio of approximately −2.6 was extrapolated for a small axial strain (less than 0.05), though we found a logarithmic decrease in Poisson's ratio to nearly −1 after just a slight increase in axial strain. According to the hinging model, the magnitude of the negative Poisson's ratio does, indeed, decline in a logarithmic fashion as ζ gets smaller for about $\zeta<40°$; however, based on the fact that the undeformed ζ in our samples was approximately 40° and the nominal axial strains applied to each sample were the same, it is likely that this particular sample had some inherent mechanical discrepancies introduced by the DMD-PP fabrication process. In could have also been possible that the scaffold was slightly compressed due to the way the sample was introduced into our strain measurement system. Nevertheless, the data for the single-layer reentrant construct aligns with the simple hinging model.

The single-layer missing rib structure demonstrated Poisson's ratios of about −0.3 to −0.5 (FIG. 3A), which showed that the Poisson's ratio stayed relatively constant for the range of axial strains tested in our experiments. Our results agree closely with the model reported by Gaspar et al., *Acta*

Mater, 52, 2439 (2005), who expanded the original missing rib model developed by Smith et al., Acta Mater, 48, 4349 (2000). Both models neglect rib stretching and bending (flexure), though each model has subtle differences. The Gaspar missing rib model was derived from engineering strain considerations and assumed hinging of the central angle α (FIG. 1B, missing rib model), i.e., $|\Delta\alpha|\geq 0$ (and $\Delta\alpha^*/\Delta\beta\geq 0$ where $\alpha^*=180-\alpha$) in addition to the hinging proposed in the Smith model. The Smith model assumed unit-cell unfolding with hinging of joint angles $\phi_1$, $\phi_2$, and β (FIG. 1B) and only rotational deformation around the central node so that $\Delta\alpha=0$ (and $\Delta\alpha^*/\Delta\beta=0$).

Examination of the optical images for the missing rib sheet (FIG. 4A), shows that there are predominately changes in $\phi_1$ and $\phi_2$ as proposed in the Smith model, with little central node hinging. For the dimensions of the missing rib structure (FIG. 1B), the Smith model predicts a $\upsilon_{xy}=-1$, overshooting Poisson's ratio by two-fold in magnitude, while the Gaspar model predicts an almost constant Poisson's ratio of −0.5 for axial strains of 0-0.2 for $\Delta\alpha^*/\Delta\beta=0.5$.

Using equation (7), angle β was calculated to have theoretically increased from 40° to approximately 55° for axial strains between 0-0.2 (changes in angle β were not measured experimentally). Because the data matches up well with the Gaspar model, skilled artisans assume some change in angle α resulting from central node hinging, and would have amounted to about one-half the change in angle β.

The single-layer intact rib constructs demonstrated experimental Poisson's ratios which varied from slightly below 0.8 to over 1.8 in an exponential fashion according to $\upsilon_{xy} \propto e^{k\epsilon_x}$ where k is the relative growth rate, and was an average of +3 in these experiments (FIG. 3A) for axial strains from approximately 0-0.2.

The Smith intact rib model yielded similar results with a k≈5 for γ of 86° and β=45° (the single-layer constructs had γ=90° and β=45° as shown in FIG. 1B), resulting in an exponential increase in Poisson's ratio from approximately 1-2.5 for the same range of axial strains as tested in our experiments. The Smith model assumes that deformation is caused solely by the hinging of angle γ with little to no rib stretching or flexure. The optical images for the intact rib sheet (FIG. 4A, lower images) appear to confirm the model as they show mostly hinging of angle γ, causing the square pore shape to become oblong.

For axial strains of 0-0.2, the Smith intact rib model yields a decrease in angle γ from 90° to approximately 65° (changes in angle γ were not measured experimentally). Though our experimental values for Poisson's ratio data (0.8-1.8) grew at a slower rate than predicted by the missing rib model, the model still appears to be a good approximation of the behavior of the single-layer constructs.

In comparing the single-layer data among the three strain tests performed for each unit-cell geometry, Poisson's ratios appeared to be consistent, as shown in FIG. 3A. Some variability existed, as expected, likely because of the fact that each experiment was performed with a different sample. Small, yet unavoidable, differences in the samples were likely introduced during DMD-PP fabrication, which would have imposed some differences in elasticity. It is also possible that the constructs experienced some minor preloading and straining when they were secured in our strain testing system, which could have affected the Poisson's ratio values at small strains. However, it is clear that geometry and spatial arrangement of the pores (unit-cell) controlled the polarity and magnitude of the Poisson's ratio of the overall meshworks, and that the strain-dependent behavior was well-predicted by stress-strain analytical models. Thus, the single-layer sheets demonstrated negative Poisson's ratios that were both determinate and tunable by virtue of their well-defined cellular meshworks.

Figure 5A:
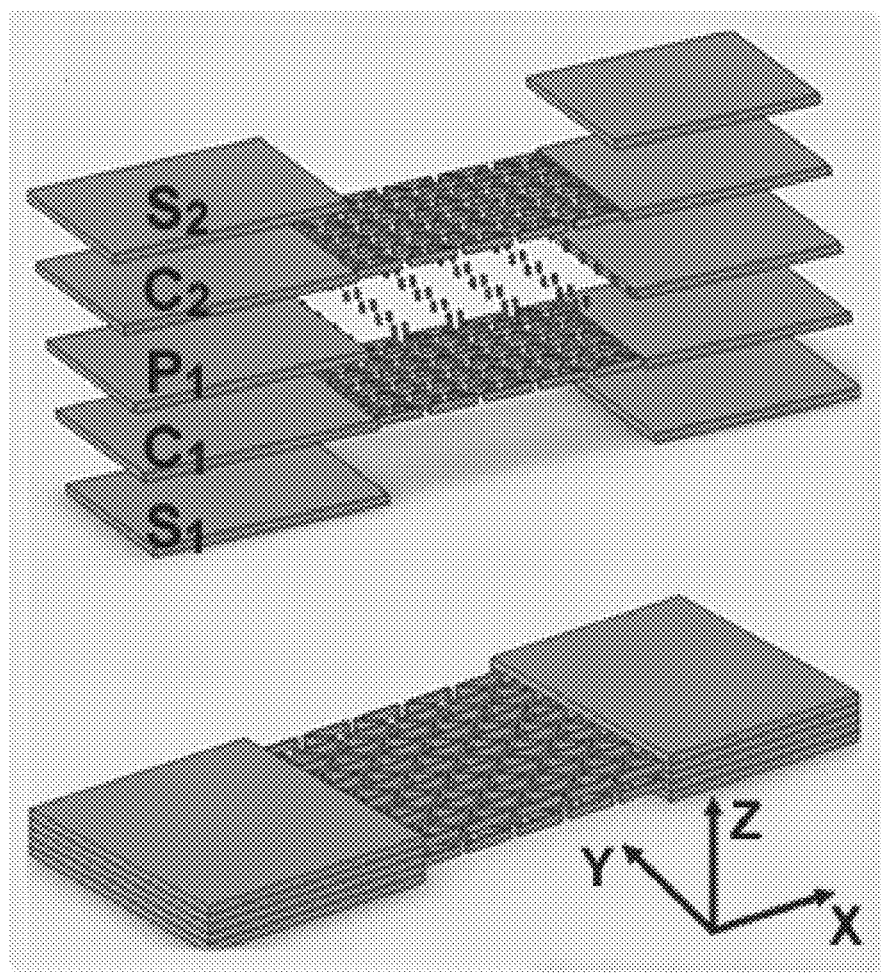
FIG. 5A is an exploded (upper) and un-exploded (lower) diagrammatic perspective view of the double-layer auxetic scaffolds assembled by stacking single-layer cellular constructs with a connecting layer of vertical posts.
Figure 5B:
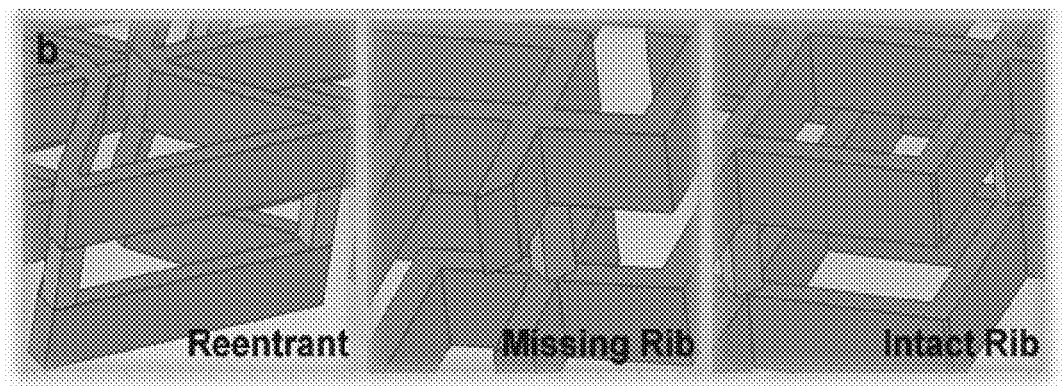
FIG. 5B provides magnified views of the double-layer stacks of the three unit cell types.

Based on the lattice meshworks of the single-layer constructs, three-dimensional biomaterial PEG scaffolds were fabricated by stacking two single-layer sheets ($C_1$ and $C_2$) with a layer of vertical posts ($P_1$), as shown in FIG. 5A. The double-layer constructs were fabricated in a layer-by-layer manner using a series of virtual photomasks in DMD-PP; each layer was approximately 100 microns thick and the rib structures were approximately 40 microns in width. FIGS. 11D and 11E are optical images of the double-layer PEG constructs synthesized with DMD-PP. FIG. 11F is and SEM image of a the double-layer hybrid PEG constructs synthesized with DMD-PP. The superimposed layers were aligned precisely on top of one another, though you can clearly see the separate layers in the magnified angle views shown in the SEM insets. As with the single-layer constructs, each layer of the multi-layer constructs had rectangular blocks that provided for mechanical support for handling and strain testing. The double-layer scaffolds have an internal pore architecture that is open to the environment and completely interconnected as desired in a tissue construct.

Strain experiments were conducted on the double-layer constructs to determine if the addition of multiple layers would alter the Poisson's ratios relative to the single-layer constructs. FIG. 12D shows the strain-dependent Poisson's ratios for the double-layer constructs for axial strains of approximately 0-0.2. Two experiments were performed for each type of construct as denoted by color. FIGS. 11D and 11E show optical images of the double-layer constructs in their undeformed and deformed states. The insets show the deformations in the individual pores. The double-layer reentrant and missing rib constructs continued to exhibit auxetic behavior while the intact rib construct persisted to show a positive Poisson's ratio.

Figure 3B:
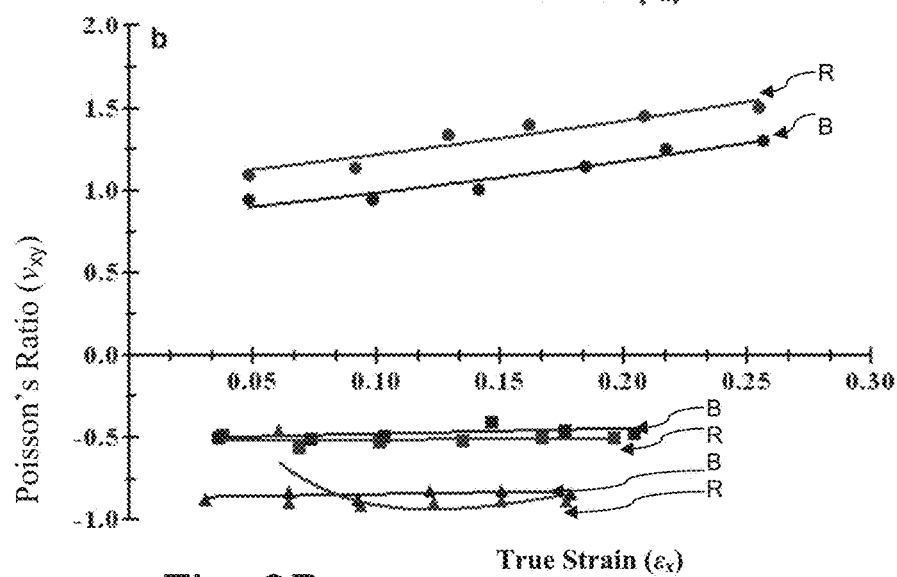

The reentrant scaffold exhibited a relatively constant Poisson's ratio of approximately −0.8 to −0.9 for strains up to slightly less than 0.20, as plotted in FIG. 3B. Two experiments were performed for each double-layer construct; each strain test was conducted with a different sample. Separate experiments are denoted by "R" and "B" in the plots, and reentrant type is indicated by a triangle (▲), missing rib type by a box (■) and intact type by a circle (●).

In one of the double-layer reentrant experiments, we found a Poisson's ratio of minus 0.5 for an axial strain of 0.05 ("R" data markers for the reentrant unit-cell, FIG. 3B). However, for a slight increase in axial strain (<0.005 increase in $\epsilon_x$), the Poisson's ratio increased (in terms of magnitude) from −0.5 to −0.9 and remained relatively stable for increasing axial strains.

Comparing the optical images of FIGS. 4A and 4B, which illustrate the single-layer and double-layer reentrant constructs respectively, the deformation of the individual pores (insets) appears very similar, in terms of the deformation mechanisms where mostly hinging of angle ζ occurs. Moreover, both auxetic layers, $C_1$ and $C_2$ (FIG. 5A), appeared to deform equally and in tandem as evident in the optical photos. There was a small discrepancy in the Poisson's ratios between the single-layer and double-layer reentrant constructs as the single-layer constructs had a Poisson's ratio that started at approximately −1 and linearly decreased to about −0.5, while the double-layer constructs demonstrated a Poisson's ratio of almost a constant −0.9. Thus, adding an additional layer did not significantly alter the strain-dependent Poisson's ratio.

The double-layer missing rib scaffold exhibited a Poisson's ratio of approximately a constant −0.5 in both strain tests (FIG. 3B). Comparing deformations in the individual pores between the single-layer and double-layer missing rib constructs shown in FIGS. 4A and 4B, the additional layer had little impact on the deformation mechanisms of the unit-cell (still mostly hinging of $\phi_1$ and $\phi_2$).

Poisson's ratios for the two intact rib experiments varied in magnitude slightly, varying from 0.9 to 1.3 in one experiment and 1.1 to 1.5 in the other, both for axial strains between 0 and 0.25 (FIG. 3B). In both strain tests of the intact rib, the Poisson's ratio increased exponentially with an average relative growth (k) of approximately +2 ($\upsilon_{xy} \propto e^{kc_x}$), which was very similar to the single-layer intact rib constructs. As was the case for the double-layer reentrant scaffold, the optical images show that the individual pores in the vertically-aligned cellular layers appeared to deform equally and in tandem (see, e.g., FIG. 4B).

Comparing the two strain tests performed for each type of double-layer scaffold, Poisson's ratio showed some variability likely due to the fact that a different scaffold was used in each test. Additionally, despite some small disparities between the Poisson's ratios of the single-layer and double-layer constructs, the addition of the second cellular layer had an insignificant influence on Poisson's ratio. This rather congruous behavior suggests that the same three-dimensional configuration (FIG. 5A) could be used to make an auxetic scaffold having more than two layers.

Figure 5C:
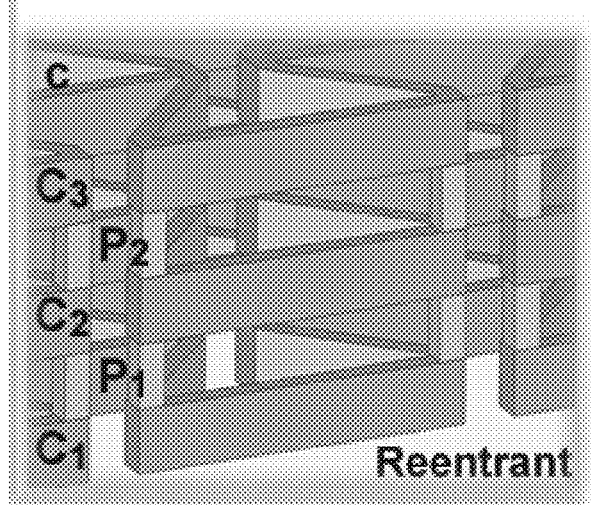
FIG. 5C is a magnified diagrammatic view of a triple-layer stack containing constructs with the reentrant pore structure.

Applying the design approach of FIG. 5A, DMD-PP was used to build a triple-layer reentrant scaffold (FIG. 5C). Three separate auxetic layers ($C_1$, $C_2$, and $C_3$) were connected by alternating layers of vertical posts ($P_1$ and $P_2$). FIGS. 2G-2I are SEM images of the triple-layer reentrant construct. As with the double-layer scaffolds, the vertical alignment of the cellular layers is precise, making it difficult to make out the multiple layers from a top view of the scaffold. However, the layers are distinguishable from the magnified angular perspectives.

Experiments demonstrating the integration of human mesenchymal stem cells (hMSCs) with the hybrid scaffolds were also carried out. Cells were found to attach to the poly(ethylene glycol)-co-acrylic acid scaffolds, with thick stress fibers visible as a result of the actin staining Interestingly, hMSCs were seen to attach to the scaffold walls and also formed sheets in and across the voids of the scaffolds (FIGS. 13A-E). This demonstrates the feasibility of utilizing the hybrid scaffolds for tissue engineering and other biological applications.

We assessed the out-of plane loading of the hybrid scaffold using a vertical custom-made stage. Out-of-plane loading on hybrid scaffold leads to conforming of only the NPR region to the bead. This demonstrates that a wound healing hybrid patch can be designed using a variety of photocurable material, with potential applications in biomedical applications which require biaxial strain characteristics (e.g. wound healing, where a hybrid patch can specifically conform to the swollen parts). Hybrid scaffolds can potentially be used for wound management applications especially for treating pressure ulcers, and hard-to-heal wounds.

Using our technique, hybrid regions can be spatially imparted a variety of hydrogels (PEG, Hyaluronic acid, Gelatin-methyacrylate), which can be loaded with a drugs and growth factors for controlled release during different wound-healing stages according to wound severity. These healing patches, can be extremely versatile, since both the elastic modulus as well as the Poisson ratio, in essence the complete elastic response, can be tailored according to the target tissue, and would likely better integrate with native tissues.

Using the technique described in this paper, we can impart a hybrid negative-positive Poisson ratio (NPR-PPR) to any photocurable biomaterial, without changing the intrinsic elastic modulus property of the biomaterial. These hybrid scaffolds are scale independent, since deformations observed in these scaffolds only depend on the geometry or architecture of the struts, which implies similar strain-dependent elastic response at various resolutions, from nano-to-macro scale. Hybrid NPR-PPR scaffolds may be more suitable for emulating the behavior of certain tissues and supporting and transmitting forces to the host site. For examples, hybrid scaffolds can be used to design arteries, since it has been shown that the sub-endothelial axially-aligned fiber layer of bovine carotid arteries behaves in a NPR or auxetic manner. Similarly, a cell-seeded heart patch with hybrid NPR-PPR property would be able to withstand the compressive and stretching forces generated during myocardial contraction (~10,000 heartbeats per day) at the suture site.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The steps depicted and/or used in methods herein may be performed in a different order than as depicted and/or stated. The steps are merely exemplary of the order these steps may occur. The steps may occur in any order that is desired such that it still performs the goals of the claimed invention.

Furthermore, although the present invention has been described in conjunction with specific embodiments thereof, it is evident that many modifications, alternatives, and variations will be apparent to those skilled in the art. Accordingly, the present invention should be construed to embrace all such modifications, alternatives, and variations that fall within the spirit and broad scope of the claims All publications, patents, and patent applications mentioned in this specification are hereby incorporated in their entirety by reference into the specification to the same extent as if each individual publication, patent, or patent application was specifically and individually indicated to be incorporated herein by reference. In addition, citation or identification of any reference in this application shall not be construed as an admission that such reference is available as prior art to the present invention.

EXAMPLE 1

Preparation of Photocurable Monomers

Poly(ethylene glycol)diacrylate (PEGDA, Mw=700), acrylic acid (AA), and 2,2,6,6-tetramethylpiperidine 1-oxyl (TEMPO, free-radical quencher) were obtained from Sigma-Aldrich. Photoinitiator Irgacure 2959 and TINUVIN 234 UV-dye were obtained from Ciba Chemistry. TINUVIN 234 is a UV-absorbing agent, which was used to reduce the curing depth of the monomers and adjust the thickness of the microstructures in the DMD-based layer-by-layer fabrication process. TEMPO, on the other hand, enhances the contrast of the UV-curing process and optimizes feature resolution at the projection plane. 1% (w/v) Irgacure 2959, 0.15% (w/v) of TINUVIN 234, and 0.01% (w/v) of TEMPO were added to the PEGDA monomer and mixed thoroughly.

EXAMPLE 2

Digital Micro-Mirror Array Device (DMD) Fabrication

Figure 6:
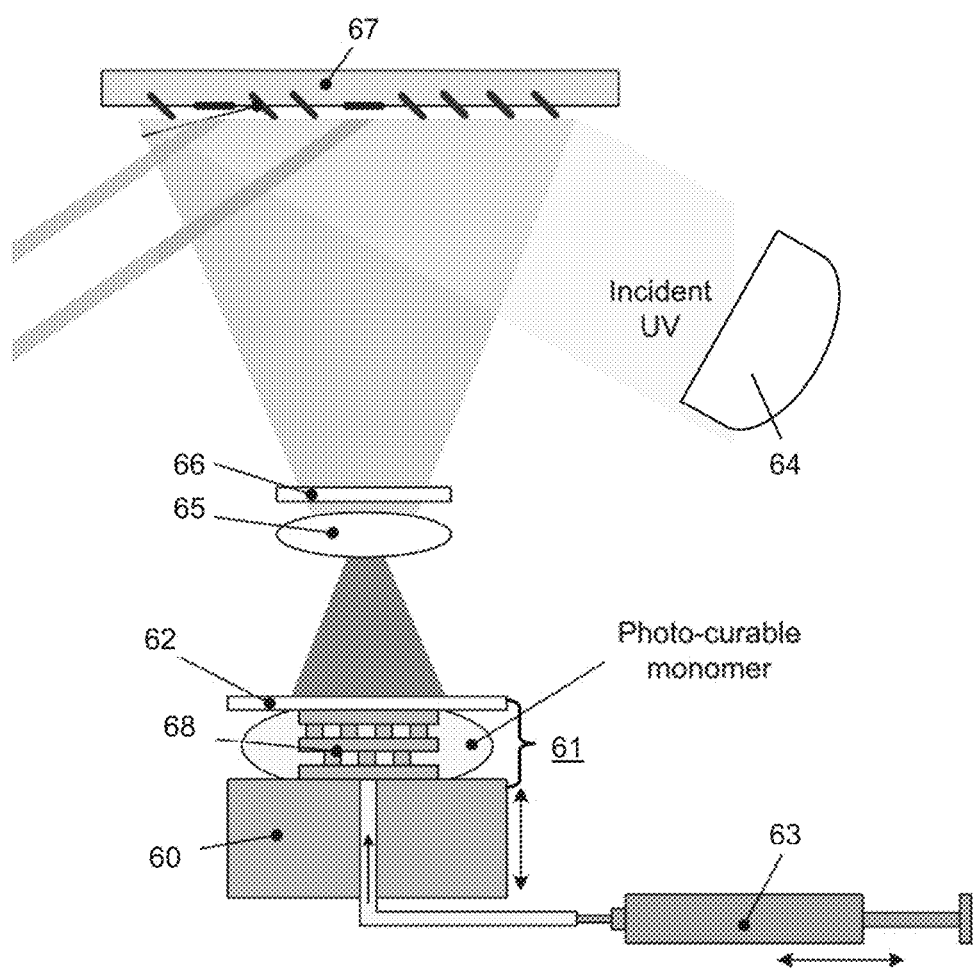
FIG. 6 illustrates a digital micro-mirror device projection printing (DMD-PP) system useful for patterning specifically-arranges unit-cellular structures to detect auxetic behavior.

FIG. 6 shows a schematic of the DMD-based system used to fabricate the auxetic biomaterial scaffolds. Two-dimensional (2D) graphics models of the scaffold layers were designed in computer-aided drafting (CAD) software (AutoCAD LT 2006; Autodesk, Inc., San Raphael, Calif., USA). CAD models in the drawing interchange format (DXF file extension, outputted from AutoCAD) were converted into standard bitmap format (BMP file extension) and exported to LabVIEW software (National Instruments, Austin, Tex., USA), which was used to control the DMD system. The bitmap graphics files were used as virtual photomasks during the DMD layer-by-layer photocuring process.

A servo-stage 60 with X, Y and Z axis motion was positioned 100 µm below a transparent quartz plate 62 (quartz microscope slide), leaving a 100 µm gap 61 between the plate and the stage. 10 µL of photocurable prepolymer was injected into the gap 61 with a syringe pump 63. The gap-spacing controlled the thickness of the photo-polymerized layer of PEG. Light emitted from the UV source 64 was focused through an iris 66 and projection lens 65 down to the projection plane, which was coplanar with the bottom side of the quartz substrate 62. The light was spatially modulated at the projection plane by a digital micro-mirror (DM) array 67 controlled by the virtual software masks. Pre-polymer was exposed with a 50 mW/cm$^2$ dose of LTV-light for 11 seconds to solidify select locations of the PEG.

After an individual layer was patterned, the stage 60 was translated downwards 300 µm, separating the solidified micropatterned sheet of PEG from the quartz substrate 62 so that it only remained attached to the servo-stage. The release process was facilitated by coating the substrate with a silane (tridecafluoro-1,1,2,2-tetrahydrooctyl-1 trichlorosilane (United Chemical Technologies, Inc., Bristol, Pa., USA), which gave the surface a low surface energy (or high contact angle). After a layer was fabricated, uncured polymer was washed away with deionized water. To create a second layer, the stage 60 was translated slightly upwards along the Z-axis until top of the previously formed structure was approximately 100 µm below the quartz substrate 62, leaving another 100-µm gap. Fresh pre-polymer was then pumped into the 100-µm gap 61, and the polymer was selectively cured using another software mask. These steps were repeated using a combination of software masks until a three-dimensional multi-layer scaffold 68 was constructed.

EXAMPLE 3

Stress-Strain Finite Element Simulations

Figure 10E:
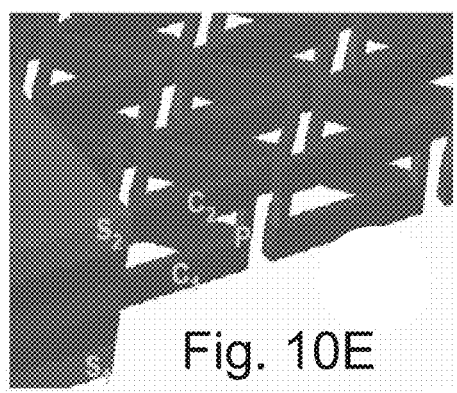
FIGS. 10E and 10F are magnified views of the double-layer stacks.
Figure 10F:
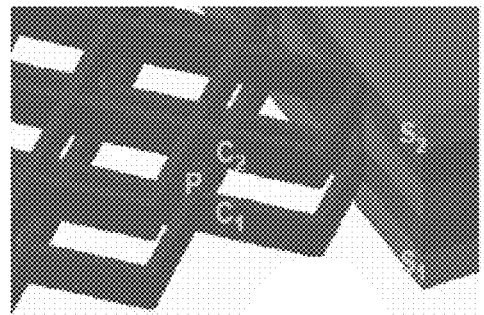
Figure 10G:
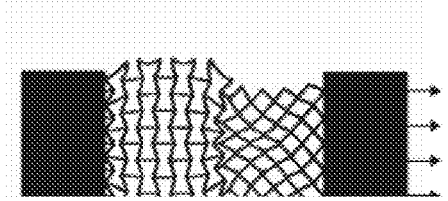
FIGS. 10G and 10H are stress-strain simulations of single and two-layer PEG scaffolds, respectively, composed of unit-cells. The walls of the unit-cells (denoted as struts) are approximately 40 microns wide and 100 microns deep.
Figure 10H:
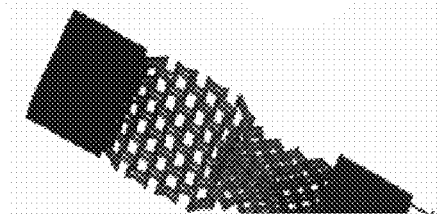

AutoCAD LT was used to design the 2D scaffold layers with the desired unit-cell structures. The unit-cell structures were designed from analytical models proposed in the literature. The 2D models were imported into SOLIDWORKS® 3D CAD software (SOLIDWORKS® 2009, Dassault Systèmes SolidWorks Corp., Concord, Mass., USA) and extruded to form 3D models of the single-layer sheets. The 3D models were utilized to simulate the elastic stress-strain (deformation) behavior of the single-layer PEG constructs using finite element analysis (also conducted with SOLIDWORKS®; FIGS. 10E and 10FA), taking into account the material properties of the PEG. The simulations allowed us to determine if the unit-cell structures would, theoretically, yield auxetic behavior as desired. The simulations were performed in the same way in which the strain experiments were conducted, i.e., where one of the rectangular side-blocks was fixed while an axial tensile stress was applied to the other rectangular block causing the scaffold to strain. 3D simulations were conducted for each unit-cell type (reentrant, missing rib, and intact rib unit-cells).

EXAMPLE 4

Strain Testing for the Determination of Poisson's Ratios

The PEG constructs were loaded into a homemade strain measurement system by fixing one of their ends on an immovable stage while fixing their other end on a movable single-axis (axial direction) nano-positioning stage. The stage was connected to a motorized servo-actuator (CMA-25CCCL Closed-Loop DC Servo-actuator, Newport Corp., Irvine, Calif., USA), which was capable of providing motion in 200-nm incremental steps. The actuator was driven and controlled by an axis-motion controller (ESP300 Axis Motion Controller and Driver, Newport Corp., Irvine, Calif., USA) that provided stable and precise movement along with a programmable Lab View interface (LabView™, National Instruments, Austin, Tex., USA).

A "pulling" axial tensile stress was applied to the end of the PEG constructs, attached to the movable stage, by the motion of the actuator while the other end of the PEG constructs, which were fixed to the immovable stage, remained still. The axial stresses exerted on the constructs ultimately caused them to strain in the axial direction. In-plane movement of the construct in the axial and transverse directions was observed with a color CCD camera system with magnifying optics (CV-S3200P CCD camera, JAI Inc., San Jose, Calif., USA; magnifying camera optics, Edmund Industrial Optics, Barrington, N.J., USA).

Still images were recorded with the CCD camera for precise levels of travel of the actuator stage. Axial and transverse strains were estimated by measuring the displacement in the axial and transverse directions, respectively. Digitizer software (GetData Graph Digitizer 2.24, getdata-graph-digitizer.com) was used to digitize the optical images so that the displacements could be accurately determined based on the under-formed in-plane dimensions of the constructs. Digitized SEM images were used to determine the under-formed dimensions.

EXAMPLE 5

Scanning Electron Microscopy (SEM)

Samples were coated with a thin 10-nm layer of platinum/palladium by sputter coating (208HR High-Resolution Sputter Coater, Cressington Scientific Instruments, Watford, England). SEM images were acquired with a Zeiss SUPRA™ 40 VP (variable pressure) Field-emission Scanning Electron Microscope at 30 kV (Zeiss SUPRA™ 40 VP FESEM, Carl Zeiss SMT Inc., Peabody, Mass., USA).

EXAMPLE 6

Calculation of Poisson's Ratios

To calculate Poisson's ratios, the overall transverse elastic deformation of the scaffolds resulting from axial strains was evaluated. Poisson's ratios using equation 1:

$$\upsilon_{xy} = -\frac{\varepsilon_y}{\varepsilon_x} \quad (1)$$

where $\varepsilon_y$ is the transverse strain resulting from an axial strain $\varepsilon_x$. The subscripts x and y denote the axial and transverse strain directions, respectively, in a two-dimensional Cartesian coordinate system with orthogonal x-axes and y-axes. In-plane values of Poisson's ratio resulting from in-plane strains were calculated. Poisson's ratio was determined from values of true strain. Total true strain ($\varepsilon_i$) was calculated by equation (2) (for any in-plane coordinate direction):

$$\varepsilon_i = \ln\left(\frac{L_i}{L_0}\right) = \sum_i \left[\ln\left(\frac{L_i}{L_{i-1}}\right) + \varepsilon_{i-1}\right] \quad (2)$$

where i=1, 2, 3, . . . , n and denotes the current strain state; $L_1$ is the current specimen length for strain state i; and $L_0$ is the initial undeformed specimen length. Total true strain was determined by summing contributions to total true strain from the application of incremental true strains. True strain was used in the calculations of Poisson's ratio, as opposed to engineering strain, due to the magnitudes of the strains involved in the experiments.

EXAMPLE 7

Unit-Cell Analytical Models

To determine how precisely the strain-dependent Poisson's ratios of a 3D PEG construct could be tuned, we compared the experimental strain data with analytical models reported in the literature. The analytical models described here contain parameters that are shown in FIG. 1B. Poisson's ratios of the biomaterial constructs was determined by measuring the overall strains in the x-direction and y-direction and did not measure changes in the internal angles of the unit-cells. To determine the deformed values of the internal angles of the unit-cells, we used our empirically-obtained values of axial strain in analytical equations relating axial strain to the deformed values of the internal angles (unless otherwise noted, all angle values reported herein have units of degrees).

The strain-angle relations for the missing and intact rib structures include constants that constrain the relations so that they yield zero axial strain for the under-formed values of the angles. The constants were determined by stipulating the initial condition that axial strain was zero for the undeformed values of the internal angles. The equations, relating axial strain to the deformed values of the internal angles in the unit-cells, were used to plot the analytical models as a function of axial strain. This made it possible to directly compare the strain-dependent rates of change of Poisson's ratio between our experimental data and the analytical functions.

For the reentrant unit-cell, the strain-dependent Poisson's ratio data was compared with the hinging model—equation (3).

$$\upsilon_{xy} = \frac{\sin\zeta^*(L_2/L_1 + \sin\zeta^*)}{\cos^2\zeta^*} \quad (3)$$

The model assumes a change in Poisson's ratio due solely to changes in angle ζ for a given set of rib lengths $L_1$ and $L_2$ (FIG. 1B). Because the strain-dependent Poisson's ratio of the reentrant hinging model is presented as a function of angle ζ, which changes as the unit-cell is axially strained, equation (4) was utilized to convert values of axial strain into deformed values of angle ζ.

$$\varepsilon_x = \ln\left(\frac{\cos\zeta^*}{\cos\zeta_0^*}\right) \quad (4)$$

where ζ*=90°−ζ. The subscript "0", represents the initial undeformed value of the angle (and does so hereafter). FIG. 7 plots Poisson's ratio as a function of true strain given by equation (3), based on the undeformed dimensions of FIG. 1B.

For the missing rib model, we compared our data to the models reported in Smith et al., *Acta Mater*, 48, 4349 (2000) and Gaspar et al., *Acta Mater.*, 53, 2439 (2005), which are shown in equations (5) and (6), respectively. The angles in the equations are based on FIG. 1B.

$$\upsilon_{xy} = -\tan(\beta)\tan(\alpha_0^* - \beta) \quad (5)$$

$$\upsilon_{xy} = -\frac{\{\cos[\alpha_0^* - \beta_0 + \Delta\beta(\kappa - 1)] - \cos(\alpha_0^* - \beta_0)\}\sin\beta_0}{(\sin\beta - \sin\beta_0)\cos(\alpha_0^* - \beta_0)} \quad (6)$$

where α*=180°−α (FIG. 1B) and κ=Δα*/Δβ in the Gaspar model, which represents hinging at the central node [equation (6)]. A few differences exist between analytical models (5) and (6). While equation (5) was derived from true (instantaneous) strain considerations, equation (6) was formulated from engineering strain, an approximation usually reserved for small strains.

Also, equation (5) assumes that only rotation occurs at the central node and excludes any hinging of the internal angle α (see FIG. 1B), i.e., Δα=0, which causes Poisson's ratio to remain constant (not strain-dependent) despite a change in angle β. On the other hand, equation (6) includes some hinging at the central node so that |Δα|≥0. Our data for Poisson's ratio matched up well with the Gaspar model given our unit-cell dimensions, which shows that some hinging likely occurs when the missing rib structure is axially strained. Equation (7) relates axial strain with deformed values of angle β.

$$\varepsilon_x = \ln|\sin\beta| + C \quad (7)$$

where C=−ln|sin $\beta_0$|=0.347|$_{\beta=45°}$.

In equation (7), constant C depends on the undeformed value of β. The constant enforces the initial condition that the axial strain is zero for the undeformed value of the angle, which was 45° for our missing rib design (FIG. 1B). FIG. 2 plots Poisson's ratio as a function of engineering strain given by equation (6), based on the undeformed dimensions of FIG. 1B. For the intact rib model, we compared our strain data with the model proposed by Smith et al., which is shown in equations (8) and (9).

$$\upsilon_{xy} = \tan^2\left(\frac{\gamma^*}{2}\right) \quad (8)$$

$$\varepsilon_X = \ln\left|\sin\left(\frac{\gamma^*}{2}\right)\right| + C \quad (9)$$

where $C = -\ln\left|\sin\left(\frac{\gamma_0^*}{2}\right)\right| = 0.347|_{\gamma=90°}$.

where $\gamma^* = 180° - \gamma$.

In equation (9), constant C depends on the undeformed value of angle γ. The constant constrains equation (9) so that it yields a zero axial strain when y equals its undeformed value, which was 90° for our structures (FIG. 1B). FIG. 2 plots Poisson's ratio as a function of true strain given by equation (8), based on the undeformed dimensions of FIG. 1B.

EXAMPLE 8

Designer Multi-Material Scaffolds of Native ECM Components Prepared by Solid Freeform Fabrication for Neural Tissue Engineering The described implementations include freeform fabrication of three-dimensional multi-material designer scaffolds as guidance conduits for tissue engineering applications. The multi-material scaffolds are fabricated with submicron scale resolution using a computer-aided layer-by-layer manufacturing system.

Multi-material systems are used to fabricate scaffold. An aqueous solution of uncrosslinked natural biopolymer with acrylated salt is prepared containing a photocrosslinker. Addition of acrylated salt to the biopolymer solution aids the fabrication process of long guidance conduits by reinforcement of the conduit during the fabrication. The photocrosslinkable moiety present in the salt gets incorporated into the scaffold during photopolymerization and adds to the stiffness of the scaffold while maintaining the submicron scale resolution.

A computer-aided, layer-by-layer manufacturing system is employed to fabricate the scaffold by photopolymerization of uncrosslinked monomer solution (e.g., hyaluronic acid). The system uses a dynamic mask for photopolymerization of an entire polymer layer simultaneously. Therefore, addition of acrylated salt (i.e. zinc acrylate) aids the fabrication of long 3D guidance conduits with complex nerve mimicking microarchitecture in a layer-by-layer fashion without breaking the conduit. The scaffold is washed after fabrication to get rid of uncrosslinked components and ions (zinc). The end result is a multi-material scaffold with complex architecture for tissue engineering applications.

The system also exhibits the capability of fabricating scaffolds with spatially localized microenvironment of bioactive factors and extracellular matrix components. By localizing different growth factors in each layer, or within partial layers, one would achieve precise spatial patterning of biochemical microenvironments inside the nerve conduit. It also gives the feasibility of creating gradients of bioactive factors which can enhance the axonal regeneration and neurite extension leading to functional reinnervation.

The multi-material nerve engineering scaffolds obtained by the solid freeform fabrication method can be used as materials for tissue engineering devices. The designer structure of the scaffold such as branched conduits, conduits with multiple channels, conduits with localized microenvironments of biochemical factors resemble the complex neural microarchitecture found in natural nerve tissues such as nerve fascicles and branched nerves. These scaffolds with neural microarchitecture can guide the infiltration of cells, neurite outgrowth and vascularization into biomimetic patterns.

The features of the method are that the nerve mimicking complex designer scaffold is fabricated using a biopolymer which is a native ECM component and a photocrosslinkable salt that imparts mechanical stiffness to the scaffold.

This technique allows the scaffold can be fabricated as conduits with multi-channels and branches which mimics the neural microarchitecture and works with biopolymers. Addition of acrylated salt results in reinforcement of scaffold which makes it amenable to fabricate longer conduits (with channels or branches) with submicron scale resolution without breaking the conduit. Growth factors and ECM components can be spatially localized in different layers or regions of the scaffold resulting in spatial patterning of biochemical microenvironments.

This solid freeform-fabrication method is designed specifically for biopolymers and forms three dimensional multi-material patterned scaffolds. Multi-lumen conduit and branched structures can be created with fine precision with spatially localized biochemical microenvironment, thus permitting the creation of biopolymer scaffolds with branched conduits and lumens allows for the mimic of most natural tissue, which contain microvasculature and neuronal architecture in the shape of oriented, highly branched and multi-lumen patterns.

The inventive method is also capable of creating microenvironments of spatially localized biomolecules. Multi-material tissue engineered constructs fabricated by solid freeform fabrication are ideal for guiding cellular infiltration, vascularization, neuronal growth and functional reinnervation.

This scaffold can be created with multiple lumens, branches resembling natural nerves and works with biopolymers. The photocrosslinkable salt imparts mechanical stiffness to the scaffold which makes it amenable to create longer conduits without breakage and the scaffold can be created with very fine and intricate morphologies as are found in biological tissues.

EXAMPLE 9

Designer Multi-Material Scaffolds of Native ECM Components Prepare by Solid Freeform Fabrication for Neural Tissue Engineering The fundamental goal of tissue engineering is to create materials that can replace or repair injured tissues. To that end it is desirable to have tissue engineered constructs that mimic the architecture of native tissues. Provided herein are novel 3D guidance conduits of natural biopolymers with intraluminal channels using the solid free-form fabrication system. This approach offers tremendous flexibility to create designer scaffolds such as branched tubes (to mimic branched nerves at a plexus) and, gradients of various biomolecules.

The method of creating 3D designer scaffolds works with natural biopolymers such as hyaluronic acid which have long established records as tissue engineering materials. The microarchitecture of the scaffold mimics the structure of native nerve, has spatially localized microenvironment of bioactive molecules.

The multi-lumen and branched scaffolds can be used as materials for tissue engineering devices. The lumen of the conduit resembles the fine and intricate structures found in natural tissues such as microvessels and neural fascicles. These scaffolds can guide the infiltration of cells, neurite outgrowth and vascularization into biomimetic patterns.

EXAMPLE 10

A Sacrificial Material for Organic-Based, 3-Dimensional Fabrication

Figure 8A:
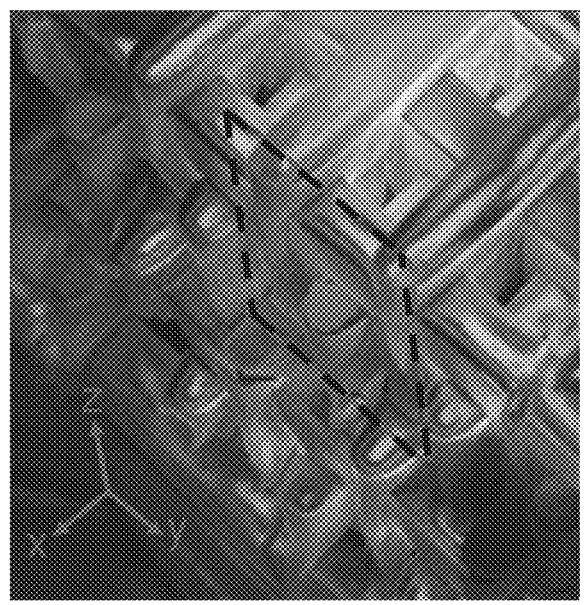
FIG. 8A shows an SEM picture of a 3D micro-scaffold (wood-pile) made by poly-ethylene-glycol using DMD-PP. While the resolution at XY plane reaches a few micrometers, the Z-resolution cannot be effectively controlled.

Described herein is a sacrificial-material for building organic-based, 3-dimensional (3D) micro-structures and also its synthesis. 3-dimensional (3D), organic-based micromachining is important to several rapidly emerging technologies, such as biomedical tissue engineering and fuel cells, where microstructures are built using a large variety of organic chemicals. An effective sacrificial material is critical for these emerging fields. Without sacrificial materials, the resolution of organic-based micromachining along the Z-axis is limited. The SEM image of FIG. 8A shows an organic woodpile microstructure, which was formed by patterning a photo-curable material with multiple photo-masks.

Viewed from the top, the microstructure has a resolution of several microns, because the features in the X-Y plane were directly patterned by the photo-masks, which have sub-micron resolutions. However, the minimum feature along the Z-axis of the microstructure is in the tens of microns, and depends on the curing depth of the photo-curable material. The Z-resolution is difficult to control unless a sacrificial material becomes available for the micro-machining Lacking sacrificial material also limits the geometries that organic materials can build.

Figure 8B:
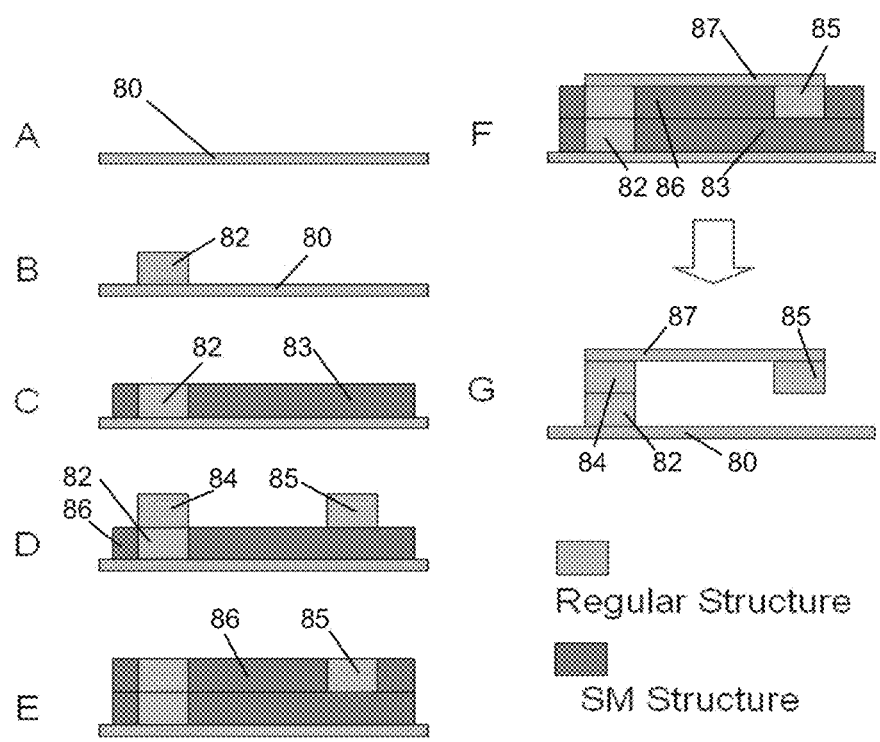
FIG. 8B illustrates a series of steps for constructing a hanging structure according to the present invention.

An exemplary sequence for controlling Z-resolution to construct "hanging" using sacrificial material is shown in FIG. 8B. The base 80 in step A has a vertical structure (post) 82 formed in step B, followed by injection of a sacrificial material 83 to fill the area around the post 82 in step C. In step D, a second post 84 is formed on top of the first post 82 along with a separate post 85, which is formed on top of the sacrificial material 83. In step E, more sacrificial material 86 is added to fill in the areas around the posts 84 and 85. A planar structure 87 is formed on top of posts 84,85 and sacrificial material 86 in step F, after which the sacrificial material is removed in step G, leaving the handing structure.

EXAMPLE 11

Figure 9:
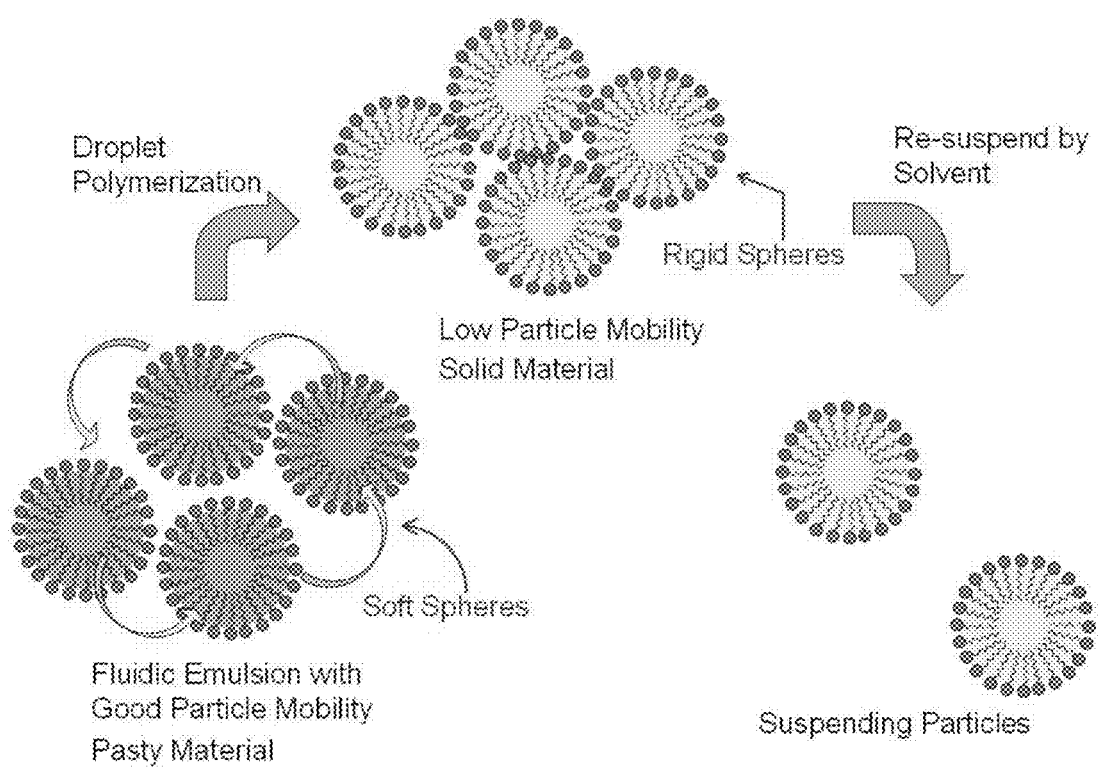
FIG. 9 demonstrates an emulsion formed by close-packed micro-droplets becomes solidified after polymerization take place in the droplets. A solvent strong to the suspending liquid can re-suspend the droplets and dissolve the cured emulsion.

Sacrificial Material (FIG. 9)

A sacrificial material described and useful herein is a curable emulsion (FIG. 9) formed by mixing two immiscible liquids using a surfactant. The two immiscible liquids are one supportive liquid and one droplet-forming liquid. The droplet-forming liquid forms close-packed micron-scaled droplets in the supportive liquid. The surfactant keeps the droplets separated and thus stabilizes the emulsion.

The surfactant includes one amphiphilic molecule which has two sites: one site-for-droplet-attaching and one site-for-supportive-liquid-attaching. The site-for-droplet-attaching is affinitive to the droplet-forming liquid and the site-for-supportive-liquid-attaching is affinitive to the supportive liquid.

The droplet-forming liquid includes a polymerizing material. Upon polymerization, the polymerizing material increases the viscosity/rigidity of the droplets and solidifies the emulsion. The surfactant keeps the droplets separated before and after polymerization. A solvent for the supportive-liquid can penetrate the cured emulsion and re-suspend the droplets, dissolving the sacrificial material.

Each molecule of the polymerizable material contains at least one active group, selected from a list including acrylate, methacrylate, epoxy, carboxylic group, and amino group. Besides the polymerizable material, the droplet-forming liquid may also contain an initiator, which induces crosslinking among the active groups. The initiator is selected from a list including photo-free-radical-generator, thermal-free-radical-generator, photo-acid-generator, thermal-acid-generator, photo-base-generator, and thermal-base-generator.

Also described is a method to synthesize the emulsion: mixing mechanically the droplet-forming liquid, the supportive liquid, and the surfactant. In a first embodiment, the supportive liquid is FLUORINERT® FC-40 (3M), the droplet-forming liquid includes trimethylolpropane triacrylate, the initiator is IRGACURE® 819 (Ciba), and the surfactant is perfluoro-poly(propylene glycol)-block-poly(propylene glycol)-block-perfluoro-poly(propylene glycol).

In a second embodiment, the supportive liquid is water, the droplet-forming liquid includes trimethylolpropane triacrylate, the initiator is IRGACURE® 819, and the surfactant is poly(ethylene glycol)-block-poly(propylene glycol)-block-poly(ethylene glycol).

The sacrificial material described herein is an emulsion of close-packed micro-droplets (<1 micron in diameter). Upon solidification, the mobility of the micro-droplets decreases drastically and the emulsion becomes rigid. The solidified droplets are bond together by van der Waals force but can be separated in a solvent. The sacrificial material can be removed in the solvent. Standard sacrificial materials for the industry, such as $SiO_2$ and amorphous-silicon, are homogeneous materials but not emulsions. These sacrificial materials are removed at high temperatures or in solutions of extreme PH values; the described emulsion, however, is for removal in a neutral solvent at room temperature.

As a sacrificial material to build organic microstructures, the described emulsion has the following important qualities: (1) it is a liquid; (2) it solidifies and is removable at a normal ambient condition; (3) it is chemically and physically inert to the materials at microstructures; and (4) it is removed by a solvent which do not impact the geometry stability of microstructures.

The sacrificial material described herein is a curable emulsion. The droplets in the emulsion can be polymerized under certain stimulations, such as light exposure. The application of this sacrificial material can be processed in a normal ambient condition (e.g. 1 atm, room temperature). Formed by separated micro-droplets, the solidified emulsion can be removed in a solvent.

For most organic-based materials for 3D micro-fabrication, the best supportive liquids for the emulsion are per-fluorinated liquids, for they are chemically inert and extremely immiscible with water and most organic materials. In our first embodiments, FLUORINERT® FC-40 (3M), a perfluorinated agent, was used for the supportive liquid. To prepare the surfactant, we synthesized an amphiphilic tri-block-copolymer by crosslinking KRYTOX® 157 FSL, a fluorinated poly-propylene glycol (Mn=2500, FPPG, DuPont), with poly-propylene glycol (PPG, Mn=2000, Sigma-Aldrich). The result molecule has a wide fluoro-philic site and a relatively narrow hydrocarbo-philic site, preferring to form hydrocarbon droplets (trimethylolpropane triacrylate) in a perfluorinated fluid (FC-40). Trimethylol-propane triacrylate plus 1% of photo-initiator IRGACURE® 819 (Ciba Chemistry) formed a photo-curable liquid. The emulsion was made by blending the photo-curable liquid in FC-40 with 5% surfactant. The surfactant stabilizes the close-packed droplets in FC-40. The same surfactant also keeps the droplets from crosslinking with the micro-structures. The emulsion became solid upon an exposure of ultraviolet (UV) light. A cured emulsion can be rapidly dissolved by perfluorohexane, a strong solvent to FC-40 but immiscible to most organic materials that include no fluorine atom.

The fluoro-philicity of the droplets and the supportive-liquid can be changed. For example, if a micro-structure is fabricated by using fluorinated materials, the supportive liquid should become a high-surface-tension liquid, preferably water. Also, the surfactant molecule should have a wide hydrophilic site and a narrow hydrophobic site, preferring to form organic droplets in water.

The minimum feature of a microstructure built by using this sacrificial material is limited to the diameter of the micro-droplets, which is about 0.5 micron. This emulsion is sufficient to build many kinds of 3D microstructures, such as cell-culturing scaffolds and micro-components for micro-fluidic-systems. Moreover, the material can also be used for molding in a macro-scale, 3D fabrications at macro-scales, and porous materials for chemical reactors. The same material can also be used for other macro-scaled fabrications, such as constructions, and in health-care products, such as a curable body lotion, if biocompatible materials were used.

EXAMPLE 12

A Sacrificial Material for Organic-Based, 3-Dimensional Fabrication

Described is a sacrificial material for building organic, 3-dimensional microstructures. The sacrificial material is an emulsion formed by mixing a photo-curable liquid, a per-fluorinated liquid, and a surfactant. The surfactant has a wide fluoro-philic site and a narrow hydrocarbon-philic site, which enable forming the organic droplets in the fluorinated liquid. Upon light exposure, the micro-droplets are polymerized and the emulsion becomes solid. The solidified emulsion can be a temporary molding material for micromachining The solidified emulsion can be removed by perfluorohexane, which dissolves the fluorinated liquid and re-suspends the micro-droplets.

The sacrificial material is a liquid that is removable under normal ambient conditions, chemically and physically inert with respect to the materials of microstructures, and removable by a solvent that does not affect the geometry of the organic microstructures. The sacrificial material is effective for building 3D, organic-based microstructures and can be used to manufacture bioengineering scaffolds, chemical micro-reactors, micro-fluidic channels, micro-sensors, micro-pumps, and other functional microstructures according to the present invention.

The invention claimed is:
1. A method of fabricating a microstructure biomaterial scaffold comprising:
(a) designing two-dimensional graphics models of scaffold layers;
(b) generating virtual photomasks of the scaffold layers using the designed two-dimensional graphics model; and
(c) patterning and fabricating each of the scaffold layers using the generated virtual photomasks, wherein at least one of the scaffold layers is a microstructure hybrid layer with a first portion of the microstructure hybrid layer comprising a unit-cell geometry having a negative Poisson ratio and a second portion of the microstructure hybrid layer comprising a unit-cell geometry having a positive Poisson ratio.

2. The method of claim 1, wherein the scaffold layers comprise porous layers.

3. The method of claim 2, wherein the Poisson ratio is tuned by controlling pore geometry of each scaffold layer.

4. The method of claim 2, wherein each scaffold layer is stacked above or below each other and connected by vertical connecting posts.

5. The method of claim 1, wherein each scaffold layer is stacked above or below each other and connected by vertical connecting posts.

6. A method for fabricating a microstructure biomaterial scaffold comprising:
disposing a transparent plate above a servo stage to define a gap;
injecting a photo-curable polymer into the gap;
modulating light having a wavelength suitable for curing the photo-curable polymer using a digital micro-mirror array, wherein the digital micro-mirror array is controlled by a plurality of virtual software masks for defining a microstructure pattern;
focusing modulated light onto a plane below the transparent plate to cure the photo-curable polymer within the plane with the microstructure pattern; and
removing uncured polymer to reveal a microstructure hybrid layer having the microstructure pattern, wherein at least a first portion of the microstructure hybrid layer comprises a unit-cell geometry having a negative Poisson ratio, and wherein a second portion of the microstructure hybrid layer comprises a second unit-cell geometry having a positive Poisson ratio.

7. The method of claim 6, wherein the unit-cell geometry comprises a reentrant honeycomb model.

8. The method of claim 6, wherein the unit-cell geometry comprises a cut missing rib model.

9. The method of claim 6, further comprising; after removing uncured polymer:
lowering the servo stage to define a second gap;
repeating the steps of injecting, modulating, focusing, and removing and thereby defining a second microstructure hybrid layer having a second microstructure pattern on top of the microstructure hybrid layer.

10. The method of claim 9, wherein the second microstructure layer comprises a plurality of vertical posts, and further comprising repeating the steps of injecting, modulating, focusing, and removing to define a third microstructure layer having a third microstructure pattern on top of the vertical posts.

11. The method of claim 10, further comprising:
injecting a sacrificial material into the second gap before repeating the steps of injecting, modulating, focusing, and removing; and
after the removing step, removing the sacrificial material to reveal a multi-layered microstructure.

12. The method of claim 9, wherein the step of focusing further comprises translating the servo stage in an x-y direction to cure with the microstructure pattern the photocurable polymer within one or more adjacent areas, whereby a plurality of areas are stitched together to produce a scaffold.

13. The method of claim 9, further comprising:
injecting a sacrificial material into the second gap before repeating the steps of injecting, modulating, focusing, and removing; and
after the removing step, removing the sacrificial material to reveal a multi-layered microstructure.

14. The method of claim 6, wherein the second unit-cell geometry comprises an intact rib model.

15. The method of claim 12, wherein the scaffold has a Poisson ratio tuned by controlling unit-cell geometry of each area.

16. The method of claim 6, wherein the unit-cell geometry is a reentrant six-sided honeycomb having four side angles between ribs, and wherein the negative Poisson ratio is tuned by changing one or more of the side angles and lengths of the ribs.

17. The method of claim 6, wherein the unit-cell geometry is a reentrant honeycomb having four side angles between ribs, and wherein the negative Poisson ratio is tuned by changing a direction of loading relative to an orientation of the unit-cell.

\* \* \* \* \*

UNITED STATES PATENT AND TRADEMARK OFFICE
CERTIFICATE OF CORRECTION

| | | |
|---|---|---|
| PATENT NO. | : 9,631,171 B2 | Page 1 of 1 |
| APPLICATION NO. | : 13/989024 | |
| DATED | : April 25, 2017 | |
| INVENTOR(S) | : Pranav Soman, Shaochen Chen and David Fozdar | |

It is certified that error appears in the above-identified patent and that said Letters Patent is hereby corrected as shown below:

In the Specification

Column 1, Line 15 Under GOVERNMENT RIGHTS:
Delete entire paragraph and replace with the following:
-- This invention was made with government support under DB012597 awarded by the National Institutes of Health. The government has certain rights in the invention. --

Signed and Sealed this
Tenth Day of February, 2026

John A. Squires
*Director of the United States Patent and Trademark Office*